US012656258B1

(12) United States Patent
Jha et al.

(10) Patent No.: US 12,656,258 B1
(45) Date of Patent: Jun. 16, 2026

(54) CIS,CIS-MUCONIC ACID SENSOR IN *Corynebacterium glutamicum*

(71) Applicant: Triad National Security, LLC, Los Alamos, NM (US)

(72) Inventors: Ramesh K. Jha, Los Alamos, NM (US); Taraka T. Dale, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 722 days.

(21) Appl. No.: 18/052,132

(22) Filed: Nov. 2, 2022

Related U.S. Application Data

(60) Provisional application No. 63/275,080, filed on Nov. 3, 2021.

(51) Int. Cl.

| | |
|---|---|
| ***G01N 21/64*** | (2006.01) |
| ***C12N 1/20*** | (2026.01) |
| ***C12N 15/77*** | (2006.01) |
| ***C12R 1/15*** | (2006.01) |

(52) U.S. Cl.
CPC ........... *G01N 21/6486* (2013.01); *C12N 1/20* (2013.01); *C12N 15/77* (2013.01); *C12R 2001/15* (2021.05)

(58) Field of Classification Search
CPC ...... G01N 21/6486; C12N 1/20; C12N 15/77; C12R 2001/15
See application file for complete search history.

(56) References Cited

U.S. PATENT DOCUMENTS

| | | | |
|---|---|---|---|
| 2012/0219971 | A1 | 8/2012 | Dietrich et al. |
| 2019/0367865 | A1 | 12/2019 | Johnson et al. |

OTHER PUBLICATIONS

Becker et al., "Metabolic engineering of *Corynebacterium glutamicum* for the production of cis, cis-muconic acid from lignin," *Microb Cell Fact*, 17:115, 2018 (14 pages).
Bentley et al., "Engineering glucose metabolism for enhanced muconic acid production in *Pseudomonas putida* KT2440," *Metabolic Engineering*, vol. 59, pp. 64-75, 2020.
Dale and Guss, "Agile BioFoundry—Host Onboarding and Development," *BETO Peer Review 2021*, 6 pages, Mar. 9, 2021.
Ezezika et al., "CatM Regulation of the benABCDE Operon: Functional Divergence of Two LysR-Type Paralogs in *Acinetobacter baylyi* ADP1," *Applied and Environmental Microbiology*, vol. 72, No. 3, pp. 749-1758, 2006.
Jha et al., "Engineering an *Acinetobacter* regulon for biosensing and high-throughput enzyme screening in *E. coli* via flow cytometry," *Nucleic Acids Research*, vol. 42, No. 12, pp. 8150-8160, 2014.
Kind et al., "From zero to hero—Production of bio-based nylon from renewable resources using engineered *Corynebacterium glutamicum,*" *Metabolic Engineering*, vol. 25, pp. 113-123, 2014.

*Primary Examiner* — Iqbal H Chowdhury
(74) *Attorney, Agent, or Firm* — Klarquist Sparkman, LLP

(57) ABSTRACT

Biosensors for detection of cis,cis-muconic acid and methods of their use are provided. The biosensors include a nucleic acid encoding a CatM protein operably linked to a regulatory element comprising a modified $P_{cat}$ promoter. Vectors and host cells including the biosensors are also provided.

19 Claims, 8 Drawing Sheets

Specification includes a Sequence Listing.

SEQUENCE LISTING

```
Sequence total quantity: 12
SEQ ID NO: 1            moltype = DNA  length = 138
FEATURE                 Location/Qualifiers
source                  1..138
                        mol_type = other DNA
```

-continued

```
                         organism = synthetic construct
SEQUENCE: 1
gttccattta tacgccctaa ttggttttat atacctttt agtatgcaaa aataccaaat  60
tgtttatctt ttttattatt acattaattt aaggtatgta aatagtattt attgaaaaga  120
agatggaccg atggctag                                               138

SEQ ID NO: 2             moltype = DNA  length = 138
FEATURE                  Location/Qualifiers
source                   1..138
                         mol_type = other DNA
                         organism = synthetic construct
SEQUENCE: 2
gttccattta tacgccctaa ttggttttat atacctttt agtatgcaaa aataccaaat  60
tggtgttggt ttttattatt acattaattt aaggtatgta aatagtattt attgaaaagg  120
agatggaccg atggctag                                               138

SEQ ID NO: 3             moltype = DNA  length = 138
FEATURE                  Location/Qualifiers
source                   1..138
                         mol_type = other DNA
                         organism = synthetic construct
SEQUENCE: 3
gttccattta tacgccctaa ttggttttat atacctttt agtatgcaaa aataccaaat  60
tggtatttgt ttttattatt acattcattt aaagtatgta aatagtattt attgaaaagg  120
agatatacat atggctag                                               138

SEQ ID NO: 4             moltype = DNA  length = 123
FEATURE                  Location/Qualifiers
source                   1..123
                         mol_type = other DNA
                         organism = synthetic construct
SEQUENCE: 4
ttatacgccc taattggttt tatatacctt tttagtatgc aaaaatacca aattggtatt  60
tgtttttatt attacataca tttactgtat gtaaatagta tttattgaaa aggagatata  120
cat                                                               123

SEQ ID NO: 5             moltype = DNA  length = 1035
FEATURE                  Location/Qualifiers
source                   1..1035
                         mol_type = other DNA
                         organism = synthetic construct
SEQUENCE: 5
ttattcgatg agtggcctga tatggtgcgt tgcaaacacc tcctgtacac aggcgagaat  60
tttaggaatg taattactgt ggtccatatt tcgcaccgcg agtgaaattg ggctataggc  120
atcatcatct aaaattggaa tataaagtag attcttcacc ccaatatcca tggcagacgc  180
cggtacgatg cagacgcctt cacctgctgc caccaagccg agtgccagtt gaatttctcg  240
aatttcggtg agtttggatg gtactaggcc tagttcggta aagagtgact gaataaaggt  300
cgcaaaattg ggcttttgag agactgggta cagcagcatc ggttcatcaa taatttgaga  360
gagatgaacc cctgttgctg caaactgatt gaggtgatga tgcttatgga ttgcaagttt  420
gagctgttct ttatgcaaca cgatacgtcg aattgcagga tcggtaattt tgagccgacc  480
aaaacccagg tctattttc cctgcttaag ggcattaatt tgatctttgg tgccgcattc  540
gatgagttcg atgtgaattt caggattttg ttgacgaaac agataaataa tttcaggtaa  600
caaaccatac agtaaggagc tgacgtaacc aattctcaag gtttgactga ccgttgcaat  660
ccgttttgcc attgaggacg cttgtgcagt atgagtcaaa atctgcacag catgctgata  720
aaaaaacatg cctgcttcag tcactttagc cggtctgaag ccgcgttcaa atagttggat  780
acccaattct tcttcgagtt tttgaatttg tcggctgagg ggcggctggg caatacacaa  840
cttttcagca gctttggaaa tgctttgctc ttcaaccacg gtcacaaaat atctgaggtg  900
tcttagttcc atttatacgc cctaattggt tttatatacc tttttagtat gcaaaaatac  960
caaattggta tttgttttta ttattacatt catttaaagt atgtaaatag tatttattga  1020
aaaggagata tacat                                                  1035

SEQ ID NO: 6             moltype = DNA  length = 6574
FEATURE                  Location/Qualifiers
source                   1..6574
                         mol_type = other DNA
                         organism = synthetic construct
SEQUENCE: 6
gggtatggac agttttccct ttgatatgta acggtgaaca gttgttctac ttttgtttgt  60
tagtcttgat gcttcactga tagatacaag agccataaga accgtttaaa caaacgggca  120
ctggaagggt tcttcggcca gcaaaaggcc aggaaccgta aaaaggccgc gttgctggcg  180
tttttccata ggctccgccc ccctgacgag catcacaaaa atcgacgctc aagtcagagg  240
tggcgaaacc cgacaggact ataaagatac caggcgtttc cccctggaag ctccctcgtg  300
cgctctcctg ttccgaccct gccgcttacc ggatacctgt ccgcctttct cccttcggga  360
agcgtggcgc tttctcatag ctcacgctgt aggtatctca gttcggtgta ggtcgttcgc  420
tccaagctgg gctgtgtgca cgaacccccc gttcagcccg accgctgcgc cttatccggt  480
aactatcgtc ttgagtccaa cccggtaaga cacgacttat cgccactggc agcagccact  540
ggtaacagga ttagcagagc gaggtatgta ggcggtgcta cagagttctt gaagtggtgg  600
cctaactacg gctacactag aagaacagta tttggtatct gcgctctgct gaagccagtt  660
accttcggaa aaagagttgg tagctcttga tccggcaaac aaaccaccgc tggtagcggt  720
```

```
ggttttttg tttgcaagca gcagattacg cgcagaaaaa aaggatctca agaagatcct  780
ttgatctttt ctacggggtc tgacgctcag tggaacgaaa actcacgtta agggattttg  840
gtcatgagat tatcaaaaag gatcttcacc tagatccttt tggggtgggc gaagaactcc  900
agcatgagat ccccgcgctg gaggatcatc cagccattcg ggtcgttca ctggttcccc  960
tttctgattt ctggcataga agaaccccg tgaactgtgt ggttccgggg gttgctgatt  1020
tttgcgagac ttctcgcgca attccctagc ttaggtgaaa acaccatgaa acactaggga  1080
aacacccatg aaacacccat tagggcagta gggcggcttc ttcgtctagg gcttgcattt  1140
gggcggtgat ctggtcttta gcgtgtgaaa gtgtgtcgta ggtggcgtgc tcaatgcact  1200
cgaacgtcac gtcatttacc gggtcacggt gggcaaagag aactagtggg ttagacattg  1260
ttttcctcgt tgtcggtggt ggtgagcttt tctagccgct cggtaaacgc ggcgatcatg  1320
aactcttgga ggttttcacc gttctgcatg cctgcgcgct tcatgtcctc acgtagtgcc  1380
aaaggaacgc gtgcggtgac cacgacgggc ttagcctttg cctgcgcttc tagtgcttcg  1440
atggtggctt gtgcctgcgc ttgctgcgcc tgtagtgcct gttgagcttc ttgtagttgc  1500
tgttctagct gtgccttggt tgccatgctt taagactcta gtagctttcc tgcgatatgt  1560
catgcgcatg cgtagcaaac attgtcctgc aactcattca ttatgtgcag tgctcctgtt  1620
actagtcgta catactcata tttacctagt ctgcatgcag tgcatgcaca tgcagtcatg  1680
tcgtgctaat gtgtaaaaca tgtacatgca gattgctggg ggtgcagggg gcggagccac  1740
cctgtccatg cggggtgtgg ggcttgcccc gccggtacag acagtgagca ccggggcacc  1800
tagtcgcgga taccccccct aggtatcgga cacgtaaccc tcccatgtcg atgcaaatct  1860
ttaacattga gtacgggtaa gctggcacgc atagccaagc taggcggcca ccaaacacca  1920
ctaaaaatta atagtcccta gacaagacaa acccccgtgc gagctaccaa ctcatatgca  1980
cgggggccac ataacccgaa ggggtttcaa ttgacaacca tagcactagc taagacaacg  2040
ggcacaacac ccgcacaaac tcgcactgcg caaccccgca caacatcggg tctaggtaac  2100
actgaaatag aagtgaacac ctctaaggaa ccgcaggtca atgagggttc taaggtcact  2160
cgcgctaggg cgtggcgtag gcaaaacgtc atgtacaaga tcaccaatag taaggctctg  2220
gcggggtgcc ataggtggcg cagggacgaa gctgttgcgg tgtcctggtc gtctaacggt  2280
gcttcgcagt ttgagggtct gcaaaactct cactctcgct gggggtcacc tctggctgaa  2340
ttggaagtca tgggcgaacg ccgcattgag ctggctattg ctactaagaa tcacttggcg  2400
gcgggtggcg cgctcatgat gtttgtgggc actgttcgac acaaccgctc acagtcattt  2460
gcgcaggttg aagcgggtat taagactgcg tactcttcga tggtgaaaac atctcagtgg  2520
aagaaagaac gtgcacggta cggggtggag cacacctata gtgactatga ggtcacagac  2580
tcttgggcga acggttggca cttgcaccgc aacatgctgt tgttcttgga tcgtccactg  2640
tctgacgatg aactcaaggc gtttgaggat tccatgtttt cccgctggtc tgctggtgtg  2700
gttaaggccg gtatggacgc gccactgcgt gagcacgggg tcaaacttga tcaggtgtct  2760
acctggggtg gagacgctgc gaaaatggca acctacctcg ctaagggcat gtctcaggaa  2820
ctgactggct ccgctactaa aaccgcgtct aaggggtcgt acacgccgtt tcagatgttg  2880
gatatgttgg ccgatcaaag cgacgccggc gaggatatgg acgctgtttt ggtggctcgg  2940
tggcgtgagt atgaggttgg ttctaaaaac ctgcgttcgt cctggtcacg tggggctaag  3000
cgtgctttgg gcattgatta catagacgct gatgtacgtc gtgaaatgga agaagaactg  3060
tacaagctcg ccggtctgga agcaccggaa cgggtcgaat caacccgcgt tgctgttgct  3120
ttggtgaagc ccgatgattg gaaactgatt cagtctgatt tcgcggttag gcagtacgtt  3180
ctcgattgcg tggataaggc taaggacgtg gccgctgcgc aacgtgtcgc taatgaggtg  3240
ctggcaagtc tgggtgtgga ttccaccccg tgcatgatcg ttatggatga tgtggacttg  3300
gacgcggttc tgcctactca tggggacgct actaagcgtg atctgaatgc ggcggtgttc  3360
gcgggtaatg agcagactat tcttcgcacc cactaaaagc ggcataaacc ccgttcgata  3420
ttttgtgcga tgaatttatg gtcaatgtcg cgggggcaaa ctatgatggg tcttgttgtt  3480
ggcgtcccgg aaaacgattc cgaagcccaa cctttcatag aaggcggcgg tggaatcgaa  3540
atctcgtgat ggcaggttgg gcgtcgcttg gtcggtcatt tcgaagggca ccaataactg  3600
ccttaaaaaa attacgcccc gccctgccac tcatcgcagt actgttgtaa ttcattaagc  3660
attctgccga catggaagcc atcacaaacg gcatgatgaa cctgaatcgc cagcggcatc  3720
agcaccttgt cgccttgcgt ataatatttg cccatggtga aaacgggggc gaagaagttg  3780
tccatattgg ccacgtttaa atcaaaactg gtgaaactca cccagggatt ggctgagacg  3840
aaaaacatat tctcaataaa ccctttaggg aaataggcca ggttttcacc gtaacacgcc  3900
acatcttgcg aatatatgtg tagaaactgc cggaaatcgt cgtggtattc actccagagc  3960
gatgaaaacg tttcagtttg ctcatggaaa acggtgtaac aagggtgaac actatcccat  4020
atcaccagct caccgtcttt cattgccata cgtaactccg gatgagcatt catcaggcgg  4080
gcaagaatgt gaataaaggc cggataaaac ttgtgcttat ttttctttac ggtctttaaa  4140
aaggccgtaa tatccagctg aacggtctgg ttataggtac attgagcaac tgactgaaat  4200
gcctcaaaat gttctttacg atgccattgg gatatatcaa cggtggtata tccagtgatt  4260
tttttctcca ttttagcttc cttagctcct gaaaatctcg tcgaagctcg gcggatttgt  4320
cctactcaag ctgatccgac aaaatccaca cattatccca ggtgtccgga tcggtcaaat  4380
acgctgccag ctcatagacc gtatccaaag catccggggc tgatccccgg cgccagggtg  4440
gtttttcttt tcaccagtga gacgggcaac agcatacgca aaccgcctct ccccccctccg  4500
ttgaaaacta aaaagctggg aaggtgaatc gaatttcggg gctttaaagc aaaaatgaac  4560
agcttggtct atagtggcta ggtacccttt ttgttttgga cacatgtagg gtggccgaaa  4620
caaagtatgg caggaaaaat tattcgatga gtggcctgat atggtgcgtt gcaaacacct  4680
cctgtacaca ggcgagaatt ttaggaatgt aattactgtg gtccatattt cgcaccgcga  4740
gtgaaattgg gctataggca tcatcatcta aaattggaat ataaagtaga ttcttcaccc  4800
caatatccat ggcagacgcc ggtacgatgc agacgccttc acctgctgcc accaagccga  4860
gtgccagttg aatttctcga atttcggtga gtttggatgg tactaggcct agttcggtaa  4920
agagtgactg aataaaggtc gcaaaattgg gcttttgaga gactgggtac agcagcatcg  4980
gttcatcaat aatttgagag agatgaaccc ctgttgctgc aaactgattg aggtgatgat  5040
gcttatggat tgcaagtttg agctgttctt tatgcaacac gatacgtcga attgcaggat  5100
cggtaatttt gagccgacca aaacccaggt ctatttttcc ctgcttaagg gcattaattt  5160
gatctttggt gccgcattcg atgagttcga tgtgaatttc aggattttgt tgacgaaaca  5220
gataaataat ttcaggtaac aaaccataca gtaaggagct gacgtaacca attctcaagg  5280
tttgactgac cgttgcaatc cgttttgcca ttgaggacgc ttgtgcagta tgagtcaaaa  5340
tctgcacagc atgctgataa aaaaacatgc ctgcttcagt cactttagcc ggtctgaagc  5400
cgcgttcaaa tagttggata cccaattctt cttcgagttt ttgaatttgt cggctgaggg  5460
```

-continued

```
gcggctgggc aatacacaac ttttcagcag ctttggaaat gctttgctct tcaaccacgg  5520
tcacaaaata tctgaggtgt cttagttcca tttatacgcc ctaattggtt ttatatacct  5580
ttttagtatg caaaaatacc aaattggtat ttgtttttat tattacattc atttaaagta  5640
tgtaaatagt atttattgaa aaggagatat acatatggct agcaaaggag aagaactttt  5700
cacgggagtt gtcccaattc ttgttgaatt agatggtgat gttaatgggc acaaattttc  5760
tgtccgtgga gagggtgaag gtgatgctac aaacggaaaa ctcaccctta aatttatttg  5820
cactactgga aaactacctg ttccatggcc aacacttgtc actactctga cctatggtgt  5880
tcaatgcttt tcccgttatc cggatcacat gaaacggcat gactttttca agagtgccat  5940
gcccgaaggt tatgtacagg aacgcactat atctttcaaa gatgacggga cctacaagac  6000
gcgtgctgaa gtcaagtttg aaggtgatac ccttgttaat cgtatcgagt taaagggtat  6060
tgattttaaa gaagatggaa acattcttgg acacaaactc gagtacaact ttaactcaca  6120
caatgtatac atcacggcag acaaacaaaa gaatggaatc aaagctaact tcaaaattcg  6180
ccacaacgtt gaagatggtt ccgttcaact agcagaccat tatcaacaaa atactccaat  6240
tggcgatggc cctgtccttt taccagacaa ccattacctg tcgacacaat ctgtcctttc  6300
gaaagatccc aacgaaaagc gtgaccacat ggtccttctt gagtttgtaa ctgctgctgg  6360
gattacacat ggcatggatg agctctacaa aggtggcggt tctgaattca cacctaggta  6420
accaggcatc aaataaaacg aaaggctcag tcgaaagact gggcctttcg ttttatctgt  6480
tgtttgtcgg tgaacgctct ctactagagt cacactggct caccttcggg tgggcctttc  6540
tgcgtttata gatgttggtt ctttcctaaa gttg                              6574

SEQ ID NO: 7           moltype = AA  length = 303
FEATURE                Location/Qualifiers
source                 1..303
                       mol_type = protein
                       organism = Acinetobacter baylyi
SEQUENCE: 7
MELRHLRYFV TVVEEQSISK AAEKLCIAQP PLSRQIQKLE EELGIQLFER GFRPAKVTEA  60
GMFFYQHAVQ ILTHTAQASS MAKRIATVSQ TLRIGYVSSL LYGLLPEIIY LFRQQNPEIH  120
IELIECGTKD QINALKQGKI DLGFGRLKIT DPAIRRIVLH KEQLKLAIHK HHHLNQFAAT  180
GVHLSQIIDE PMLLYPVSQK PNFATFIQSL FTELGLVPSK LTEIREIQLA LGLVAAGEGV  240
CIVPASAMDI GVKNLLYIPI LDDDAYSPIS LAVRNMDHSN YIPKILACVQ EVFATHHIRP  300
LIE                                                               303

SEQ ID NO: 8           moltype = DNA  length = 717
FEATURE                Location/Qualifiers
source                 1..717
                       mol_type = other DNA
                       organism = synthetic construct
SEQUENCE: 8
atggctagca aaggagaaga acttttcacg ggagttgtcc caattcttgt tgaattagat  60
ggtgatgtta atgggcacaa attttctgtc cgtggagagg gtgaaggtga tgctacaaac  120
ggaaaactca cccttaaatt tatttgcact actggaaaac tacctgttcc atggccaaca  180
cttgtcacta ctctgaccta tggtgttcaa tgcttttccc gttatccgga tcacatgaaa  240
cggcatgact ttttcaagag tgccatgccc gaaggttatg tacaggaacg cactatatct  300
ttcaaagatg acgggaccta caagacgcgt gctgaagtca agtttgaagg tgataccctt  360
gttaatcgta tcgagttaaa gggtattgat tttaaagaag atggaaacat tcttggacac  420
aaactcgagt acaactttaa ctcacacaat gtatacatca cggcagacaa acaaaagaat  480
ggaatcaaag ctaacttcaa aattcgccac aacgttgaag atggttccgt tcaactagca  540
gaccattatc aacaaaatac tccaattggc gatggccctg tccttttacc agacaaccat  600
tacctgtcga cacaatctgt cctttcgaaa gatcccaacg aaaagcgtga ccacatggtc  660
cttcttgagt ttgtaactgc tgctgggatt acacatggca tggatgagct ctacaaa     717

SEQ ID NO: 9           moltype = DNA  length = 34
FEATURE                Location/Qualifiers
source                 1..34
                       mol_type = other DNA
                       organism = synthetic construct
SEQUENCE: 9
gtatttgttt ttattattac attcatttaa agta                              34

SEQ ID NO: 10          moltype = DNA  length = 123
FEATURE                Location/Qualifiers
source                 1..123
                       mol_type = other DNA
                       organism = synthetic construct
SEQUENCE: 10
ttatacgccc taattggttt tatatacctt tttagtatgc aaaaatacca aattggtatt  60
tgtttttatt attacattca tttaaagtat gtaaatagta tttattgaaa aggagatata  120
cat                                                               123

SEQ ID NO: 11          moltype = DNA  length = 34
FEATURE                Location/Qualifiers
source                 1..34
                       mol_type = other DNA
                       organism = synthetic construct
SEQUENCE: 11
gtatttgttt ttattattac atacatttac tgta                              34

SEQ ID NO: 12          moltype = DNA  length = 912
```

-continued

```
FEATURE                Location/Qualifiers
source                 1..912
                       mol_type = unassigned DNA
                       organism = Acinetobacter baylyi
SEQUENCE: 12
ttattcgatg agtggcctga tatggtgcgt tgcaaacacc tcctgtacac aggcgagaat  60
tttaggaatg taattactgt ggtccatatt tcgcaccgcg agtgaaattg ggctataggc  120
atcatcatct aaaattggaa tataaagtag attcttcacc ccaatatcca tggcagacgc  180
cggtacgatg cagacgcctt cacctgctgc caccaagccg agtgccagtt gaatttctcg  240
aatttcggtg agtttggatg gtactaggcc tagttcggta aagagtgact gaataaaggt  300
cgcaaaattg ggcttttgag agactgggta cagcagcatc ggttcatcaa taatttgaga  360
gagatgaacc cctgttgctg caaactgatt gaggtgatga tgcttatgga ttgcaagttt  420
gagctgttct ttatgcaaca cgatacgtcg aattgcagga tcggtaattt tgagccgacc  480
aaaacccagg tctatttttc cctgcttaag ggcattaatt tgatctttgg tgccgcattc  540
gatgagttcg atgtgaattt caggattttg ttgacgaaac agataaataa tttcaggtaa  600
caaaccatac agtaaggagc tgacgtaacc aattctcaag gtttgactga ccgttgcaat  660
ccgttttgcc attgaggacg cttgtgcagt atgagtcaaa atctgcacag catgctgata  720
aaaaaacatg cctgcttcag tcactttagc cggtctgaag ccgcgttcaa atagttggat  780
acccaattct tcttcgagtt tttgaatttg tcggctgagg ggcggctggg caatacacaa  840
cttttcagca gctttggaaa tgctttgctc ttcaaccacg gtcacaaaat atctgaggtg  900
tcttagttcc at                                                      912
```

CIS,CIS-MUCONIC ACID SENSOR IN *Corynebacterium glutamicum*

CROSS REFERENCE TO RELATED APPLICATION

This application claims the benefit of U.S. Provisional Application No. 63/275,080 filed on Nov. 3, 2021, which is incorporated by reference herein in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure relates to biosynthesis of cis,cis-muconic acid in *Corynebacterium glutamicum*, particularly biosensors for cis,cis-muconic acid and methods of their use.

SEQUENCE LISTING INCORPORATION BY REFERENCE

The Sequence Listing is submitted as an XML file in the form of the file named 8472-107171-02_Sequence_Listing.xml, which was created on Oct. 31, 2022, and is 21,650 bytes, which is incorporated by reference herein.

BACKGROUND cis,cis-Muconic acid (muconate) is an important industrial precursor used for the production of adipic acid and terephthalic acid for nylon and polyethylene terephthalate (PET) bottles, respectively. These are presently made from petroleum. Synthetic biology and microbial engineering can be used to develop biomanufacturing of these compounds; however, in order to be competitive with conventional manufacturing, the biosynthetic route needs to be optimized, which requires capability to rapidly test large numbers of engineered strains and growth conditions.

SUMMARY

A key component in biosynthesis of plastics is production of cis,cis-muconic acid. A bottleneck in establishing such production is the lack of a high throughput screening platform for muconate production in non-model organisms, such as *Corynebacterium glutamicum*. Provided herein are biosensors for muconate that can be used in high-throughput testing of engineered microbes, in particular in engineered *Corynebacterium glutamicum*.

Provided herein in some embodiments is a cis,cis-muconic acid biosensor including a nucleic acid encoding a CatM protein operably linked to a regulatory element including a modified $P_{cat}$ promoter. The modified $P_{cat}$ promoter is capable of producing a response in the presence of ccMA or ccMA precursors (e.g., benzoate or catechol). In some examples, the modified $P_{cat}$ promoter includes a nucleic acid sequence with at least 98% sequence identity to SEQ ID NO: 9 or SEQ ID NO: 11. In some examples, the modified $P_{cat}$ promoter includes the nucleic acid sequence of SEQ ID NO: 9 or SEQ ID NO: 11. In some examples, the modified $P_{cat}$ promoter includes a nucleic acid sequence with at least 98% sequence identity to the nucleic acid sequence of SEQ ID NO: 10 or SEQ ID NO: 4.

In some embodiments, the cis,cis-muconic acid biosensor, further includes a nucleic acid encoding a reporter protein operably linked to the modified $P_{cat}$ promoter. In some examples, the reporter protein is a fluorescent protein, such as a green fluorescent protein (GFP) or superfolder GFP (sfGFP).

In some examples, the cis,cis-muconic acid biosensor includes a nucleic acid sequence with at least 90% sequence identity to SEQ ID NO: 5 or the complement thereof. In other examples, the biosensor includes or consists of the nucleic acid sequence of SEQ ID NO: 5, or the complement thereof.

Vectors including the cis,cis-muconic acid biosensor are also provided. In some embodiments, the vector includes a nucleic acid sequence with at least 98% sequence identity to SEQ ID NO: 9 or SEQ ID NO: 11 or the complement thereof. In other examples, the vector includes a nucleic acid with at least 98% sequence identity to SEQ ID NO: 10 or SEQ ID NO: 4 or the complement thereof. In further examples, the vector includes a nucleic acid sequence with at least 90% sequence identity to SEQ ID NO: 5 or the complement thereof. In one example, the vector includes or consists of the nucleic acid sequence of SEQ ID NO: 6.

Also provided are hosts cells including a disclosed cis,cis-muconic acid biosensor or vectors including a disclosed cis,cis-muconic acid biosensor. In some examples, the host cell is a bacterial cell, such as a *Corynebacterium glutamicum* cell. In other examples, the cell includes an inactive or deleted catB gene, an overexpressed catA gene, or both.

Methods of detecting cis,cis-muconic acid utilizing the disclosed biosensors are also provided. In some embodiments, the methods include culturing a host cell including or expressing a cis,cis-muconic acid biosensor under conditions sufficient to detect cis,cis-muconic acid (such as conditions sufficient to produce cis,cis-muconic acid) and detecting output of a reporter. In some examples, the reporter is a fluorescent protein, and detecting the output is by detecting fluorescent signal (for example, using flow cytometry or a fluorescence microplate reader). In some examples, the cis,cis-muconic acid is produced by the cell. In other examples, the cis,cis-muconic acid is produced outside the cell (for example, in the environment of the cell). The host cell may also express a transporter capable of transporting cis,cis-muconic acid into the host cell (such as a heterologous, modified, or overexpressed transporter). In some embodiments, the methods the genome of the host cell is mutated, for example, to generate a population of cells with a plurality of genotypic variants.

The foregoing and other features of the disclosure will become more apparent from the following detailed description, which proceeds with reference to the accompanying figures.

$P_{cat}$ sequence optimized for *C. glutamicum* ($P_{cat}$-opt-2; SEQ ID NO: 3). Identified variations from native promoter are represented in bold font. Newly identified variant nucleotides in $P_{cat}$-opt-2 are marked with arrows.

Figure 3:
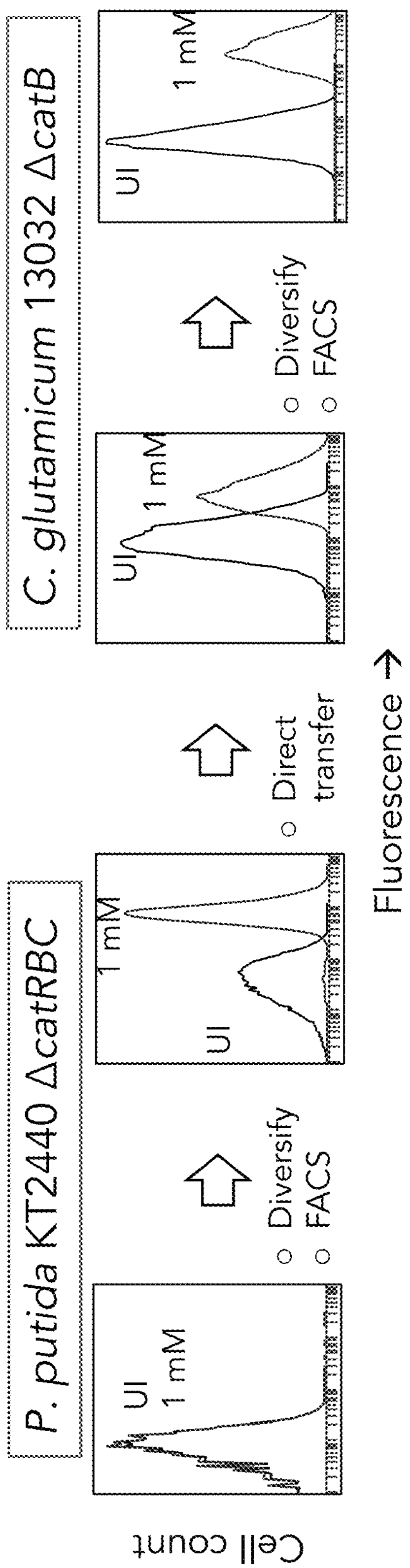

FIG. 3 shows detection of muconate in *P. putida* and *C. glutamicum*. In *P. putida*, with the *A. baylyi* native $P_{cat}$ promoter no response to 1 mM benzoate (a precursor of muconate) was detected, while strong response was detected with $P_{cat}$-opt-1 (left panel). In *C. glutamicum*, $P_{cat}$-opt-1 showed higher background and lower contrast ratio, but $P_{cat}$-opt-2 provided lower background and higher contrast ratio (right panel).

Figure 4A:
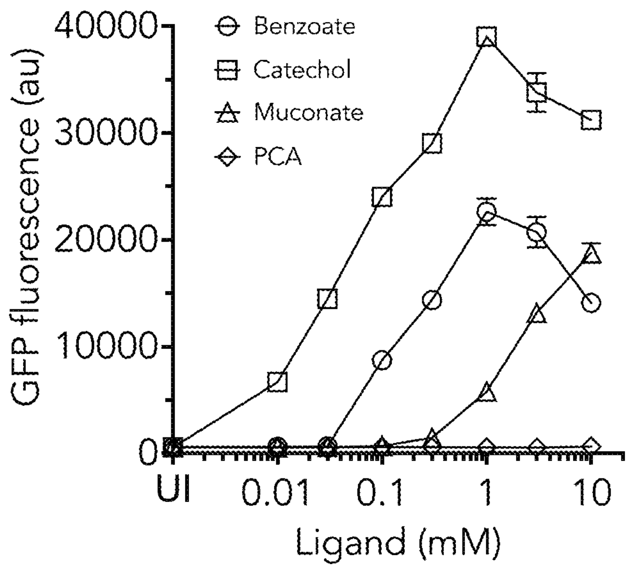
Figure 4B:
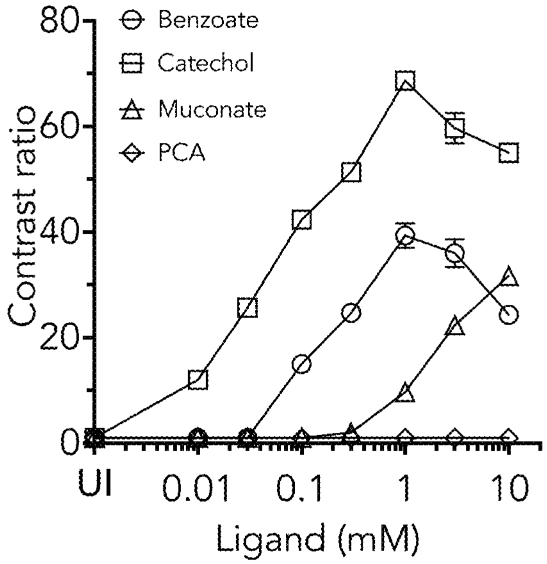

FIGS. 4A and 4B show induction of biosensor fluorescence by different inducers. Muconate is the native inducer of CatM. Benzoate and catechol are precursors of muconate in *C. glutamicum*. Protocatechuate (PCA) is a negative control and cannot be routed to muconate in *C. glutamicum*. FIGS. 4A and 4B show raw fluorescence and fold-change, respectively. The data represent mean values with standard deviation shown as error bars from three biological replicates.

Figure 5A:
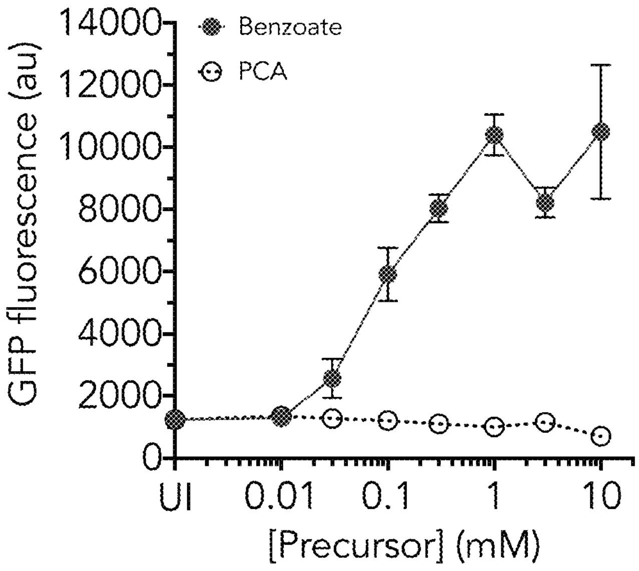
Figure 5B:
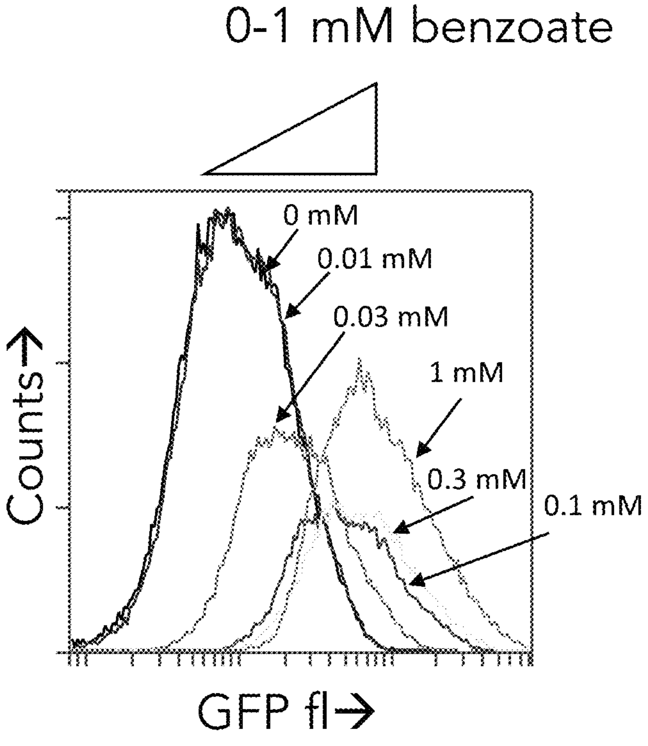

FIGS. 5A and 5B show activity of *P. putida* optimized ccMA biosensor in *C. glutamicum* 13032 (AcatB). FIG. 5A shows biosensor response to Benzoate (ccMA precursor) and PCA (negative control). FIG. 5B shows fluorescence histogram plotted by flow cytometer at increasing benzoate concentration.

Figure 6:
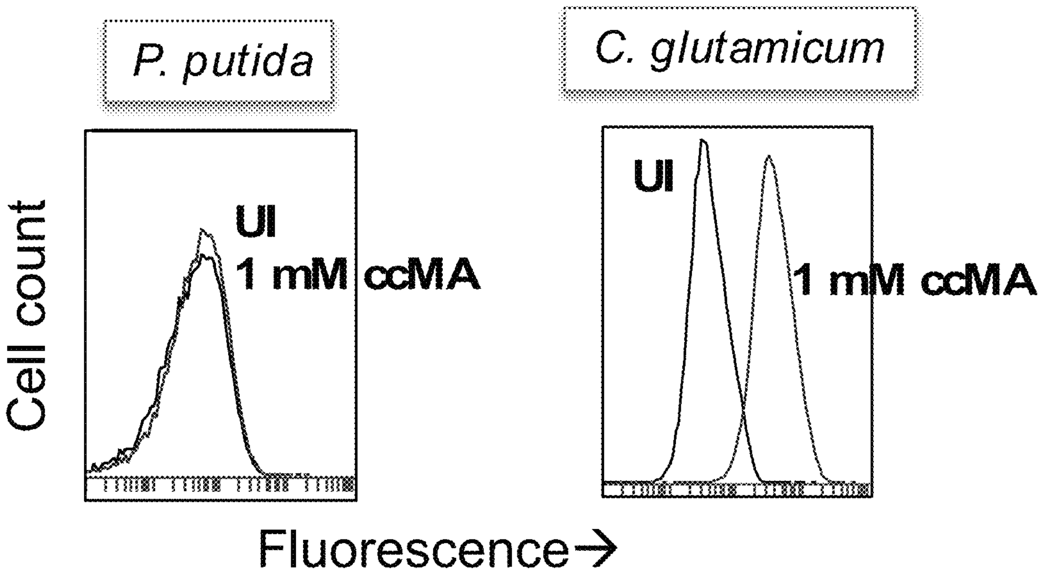

FIG. 6 shows ccMA sensing in *P. putida* KT2440 (left) and *C. glutamicum* 13032 (right). The strains with deleted catB gene to eliminate ccMA catabolismand transformed with optimized biosensor (pCatM_C2 for KT2440 and pRJ2010 for 13032). The cell population shifts to high GFP fluorescence only in case of 13032.

Figure 7:
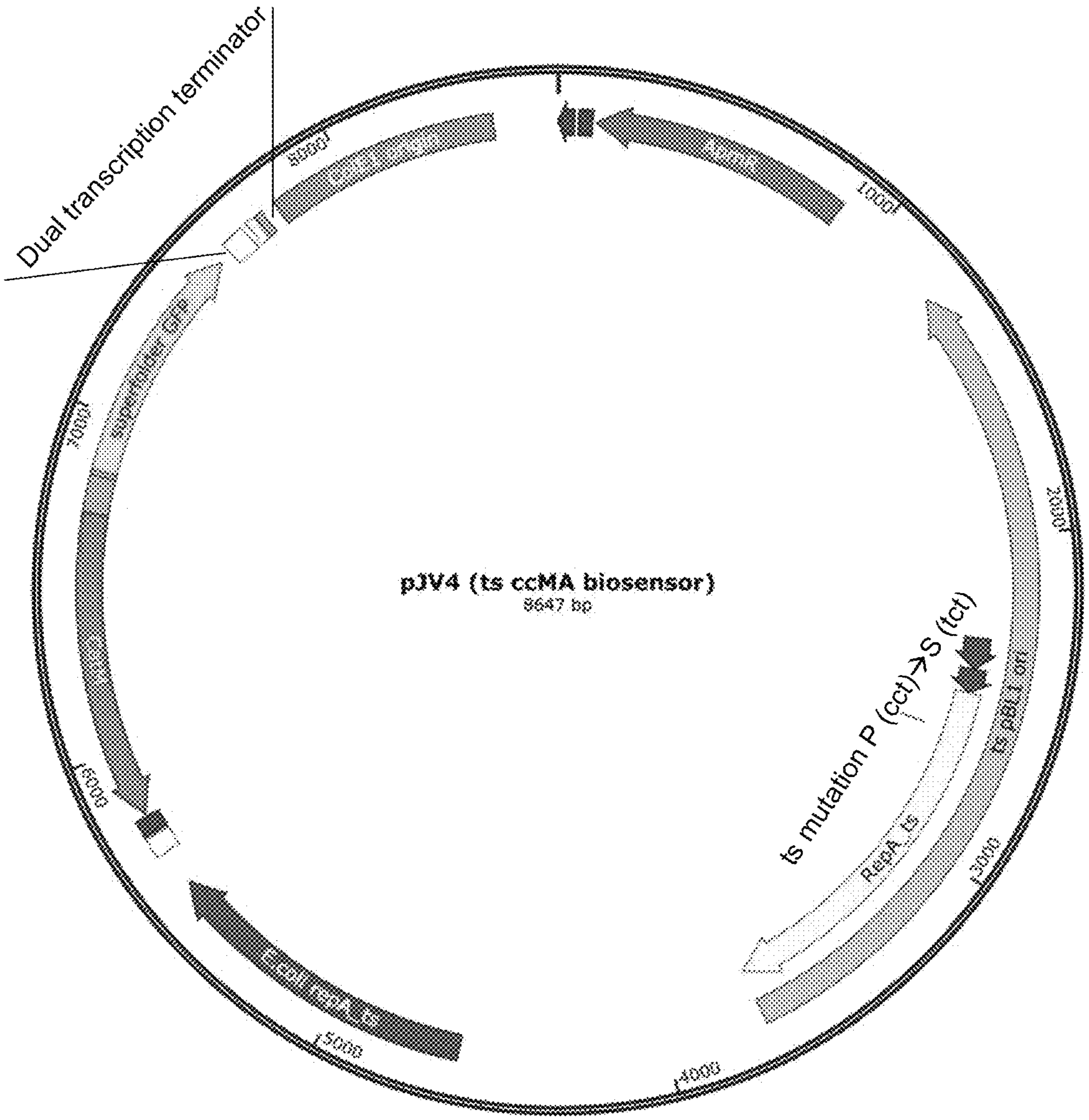

FIG. 7 is a schematic diagram of a temperature sensitive (ts) plasmid construct with ccMA biosensor cassette. The backbone pMB1/bla was used to insert RepA_ts and apramycin resistance gene marker (ApmR). The ccMA biosensor cassette including catM, $P_{cat}$-opt-2 and sfgfp sequences were inserted in the vector to create a temperature sensitive ccMA biosensor.

Figures 8A, 8B, 8C, 8D, 8E, 8F:
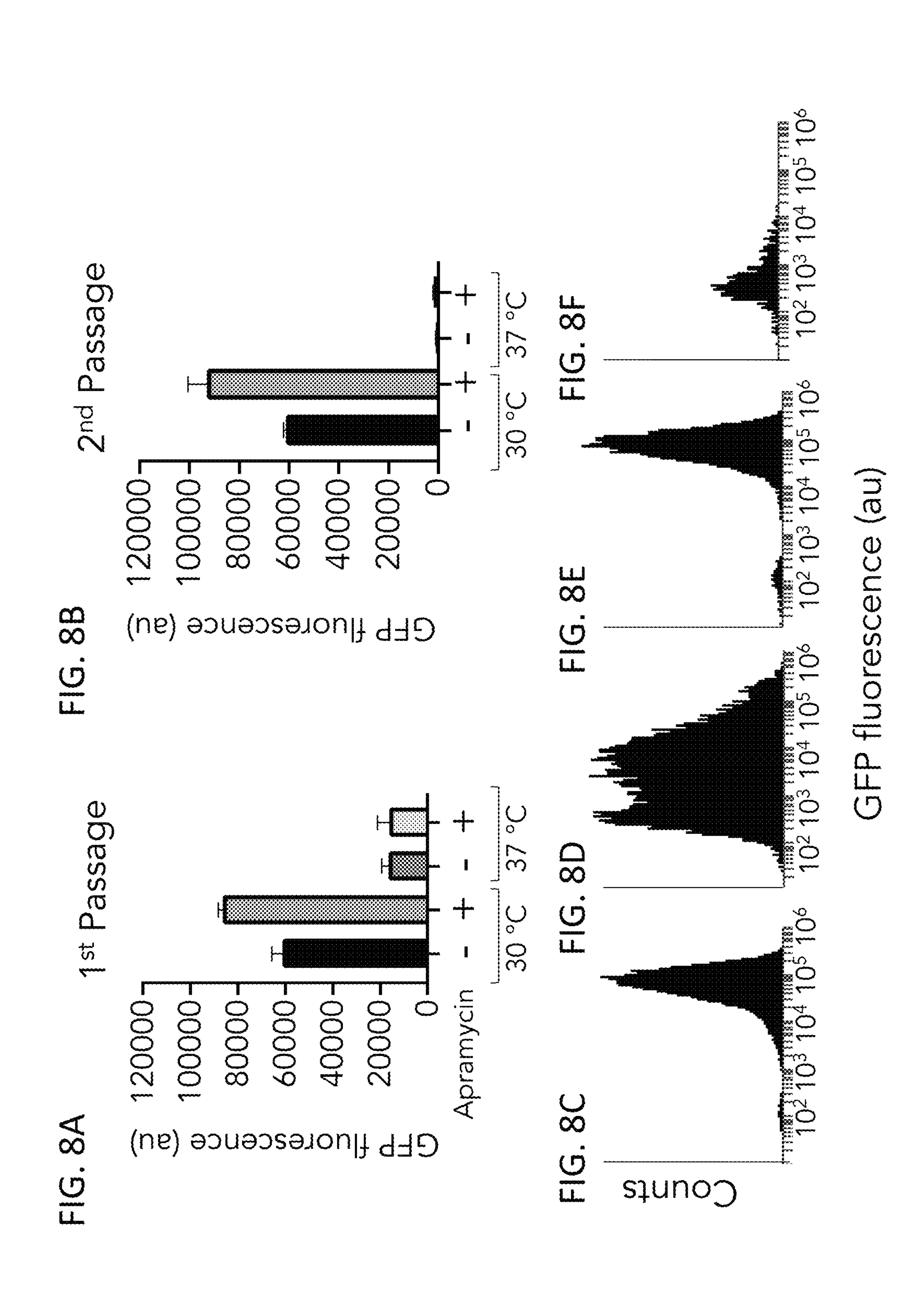

FIGS. 8A-8F show development of a temperature sensitive (ts) ccMA biosensor in *C. glutamicum* 13032 for rapid curing. FIG. 8A shows first round of growth and induction of 13032 ΔcatB strain harboring ts ccMA biosensor, pJV4. The biosensor includes an apramycin resistance gene. Induction was performed using 1 mM catechol and the cells were grown at 30 or 37° C. in the presence or absence of apramycin. FIG. 8B shows second round of growth and induction while maintaining the same condition as the first round. FIG. 8C shows 13032 after first passage and grown at 30° C. with apramycin. FIG. 8D shows after first passage and grown at 37° C., no apramycin. FIG. 8E shows after second passage and grown at 30° C. with apramycin. FIG. 8F shows after second passage and grown at 37° C., no apramycin. The histograms in FIGS. 8C-8F were generated by BD Accuri C6 flow cytometer.

SEQUENCE LISTING

Any nucleic acid and amino acid sequences listed herein and in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is a nucleic acid sequence including the sequence of a native *Acinetobacter baylyi* ADP1 $P_{cat}$ promoter (uppercase text) and flanking regions (lowercase text).

gttccatTTATACGCCCTAATTGGTTTTATATACCTTTTTAGTATGCAAA

AATACCAAATTGTTTATCTTTTTTATTATTACATTAATTTAAGGTATGTA

AATAGTATTTATTGAAAAGAAGATGGACCGatggctag

SEQ ID NO: 4 is a nucleic acid sequence including the sequence of an alternate exemplary $P_{cat}$ promoter optimized for *C. glutamicum*.

TTATACGCCCTAATTGGTTTTATATACCTTTTTAGTATGCAAAAATACCA

AATTGGTATTTGTTTTTATTATTACATACATTTACTGTATGTAAATAGTA

TTTATTGAAAAGGAGATATACAT

SEQ ID NO: 2 is a nucleic acid sequence including the sequence of $P_{cat}$-opt-1, a $P_{cat}$ promoter optimized for *Pseudomonas putida* (uppercase text) and flanking regions (lowercase text).

gttccatTTATACGCCCTAATTGGTTTTATATACCTTTTTAGTATGCAAA

AATACCAAATTGGTGTTGGTTTTTATTATTACATTAATTTAAGGTATGTA

AATAGTATTTATTGAAAAGGAGATGGACCGatggctag

SEQ ID NO: 3 is a nucleic acid sequence including the sequence of $P_{cat}$-opt-2, an exemplary $P_{cat}$ promoter optimized for *C. glutamicum* (uppercase text) and flanking regions (lowercase text).

gttccatTTATACGCCCTAATTGGTTTTATATACCTTTTTAGTATGCAAA

AATACCAAATTGGTATTTGTTTTTATTATTACATTCATTTAAAGTATGTA

AATAGTATTTATTGAAAAGGAGATATACATatggctag

SEQ ID NO: 5 is the nucleic acid sequence of an exemplary cis,cis-muconic acid sensor. Underlined text: catM; bold text: modified $P_{cat}$ promoter ($P_{cat}$-opt-2).

TTATTCGATGAGTGGCCTGATATGGTGCGTTGCAAACACCTCCTGTACAC

AGGCGAGAATTTTAGGAATGTAATTACTGTGGTCCATATTTCGCACCGCG

AGTGAAATTGGGCTATAGGCATCATCATCTAAAATTGGAATATAAAGTAG

ATTCTTCACCCCAATATCCATGGCAGACGCCGGTACGATGCAGACGCCTT

CACCTGCTGCCACCAAGCCGAGTGCCAGTTGAATTTCTCGAATTTCGGTG

AGTTTGGATGGTACTAGGCCTAGTTCGGTAAAGAGTGACTGAATAAAGGT

CGCAAAATTGGGCTTTTGAGAGACTGGGTACAGCAGCATCGGTTCATCAA

TAATTTGAGAGAGATGAACCCCTGTTGCTGCAAACTGATTGAGGTGATGA

TGCTTATGGATTGCAAGTTTGAGCTGTTCTTTATGCAACACGATACGTCG

AATTGCAGGATCGGTAATTTTGAGCCGACCAAAACCCAGGTCTATTTTTC

CCTGCTTAAGGGCATTAATTTGATCTTTGGTGCCGCATTCGATGAGTTCG

ATGTGAATTTCAGGATTTTGTTGACGAAACAGATAAATAATTTCAGGTAA

CAAACCATACAGTAAGGAGCTGACGTAACCAATTCTCAAGGTTTGACTGA

-continued

CCGTTGCAATCCGTTTTGCCATTGAGGACGCTTGTGCAGTATGAGTCAAA

ATCTGCACAGCATGCTGATAAAAAAACATGCCTGCTTCAGTCACTTTAGC

CGGTCTGAAGCCGCGTTCAAATAGTTGGATACCCAATTCTTCTTCGAGTT

TTTGAATTTGTCGGCTGAGGGGCGGCTGGGCAATACACAACTTTTCAGCA

GCTTTGGAAATGCTTTGCTCTTCAACCACGGTCACAAAATATCTGAGGTG

-continued

TCTTAGTTCCATTTATACGCCCTAATTGGTTTTATATACCTTTTTAGTAT

GCAAAAATACCAAATTGGTATTTGTTTTTATTATTACATTCATTTAAAGT

ATGTAAATAGTATTTATTGAAAAGGAGATATACAT

SEQ ID NO: 6 is the nucleic acid sequence of an exemplary vector (pRJ2010) including a cis,cis-muconic acid biosensor. Underlined text: catM; bold text: modified Pour promoter (Pour-opt-2); italic text: sfgfp reporter.

GGGTATGGACAGTTTTCCCTTTGATATGTAACGGTGAACAGTTGTTCTACTTTTGTTTGTTAGTCTTGAT

GCTTCACTGATAGATACAAGAGCCATAAGAACCGTTTAAACAAACGGGCACTGGAAGGGTTCTTCGGCCA

GCAAAAGGCCAGGAACCGTAAAAAGGCCGCGTTGCTGGCGTTTTTCCATAGGCTCCGCCCCCCTGACGAG

CATCACAAAAATCGACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCTGTCCGCCTTTCT

CCCTTCGGGAAGCGTGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCCGGTAACTATCGTC

TTGAGTCCAACCCGGTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACACTAGAAGAACAGTA

TTTGGTATCTGCGCTCTGCTGAAGCCAGTTACCTTCGGAAAAAGAGTTGGTAGCTCTTGATCCGGCAAAC

AAACCACCGCTGGTAGCGGTGGTTTTTTTGTTTGCAAGCAGCAGATTACGCGCAGAAAAAAAGGATCTCA

AGAAGATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTGGGGTGGGCGAAGAACTCCAGCATGAGAT

CCCCGCGCTGGAGGATCATCCAGCCATTCGGGGTCGTTCACTGGTTCCCCTTTCTGATTTCTGGCATAGA

AGAACCCCCGTGAACTGTGTGGTTCCGGGGGTTGCTGATTTTTGCGAGACTTCTCGCGCAATTCCCTAGC

TTAGGTGAAAACACCATGAAACACTAGGGAAACACCCATGAAACACCCATTAGGGCAGTAGGGCGGCTTC

TTCGTCTAGGGCTTGCATTTGGGCGGTGATCTGGTCTTTAGCGTGTGAAAGTGTGTCGTAGGTGGCGTGC

TCAATGCACTCGAACGTCACGTCATTTACCGGGTCACGGTGGGCAAAGAGAACTAGTGGGTTAGACATTG

TTTTCCTCGTTGTCGGTGGTGGTGAGCTTTTCTAGCCGCTCGGTAAACGCGGCGATCATGAACTCTTGGA

GGTTTTCACCGTTCTGCATGCCTGCGCGCTTCATGTCCTCACGTAGTGCCAAAGGAACGCGTGCGGTGAC

CACGACGGGCTTAGCCTTTGCCTGCGCTTCTAGTGCTTCGATGGTGGCTTGTGCCTGCGCTTGCTGCGCC

TGTAGTGCCTGTTGAGCTTCTTGTAGTTGCTGTTCTAGCTGTGCCTTGGTTGCCATGCTTTAAGACTCTA

GTAGCTTTCCTGCGATATGTCATGCGCATGCGTAGCAAACATTGTCCTGCAACTCATTCATTATGTGCAG

TGCTCCTGTTACTAGTCGTACATACTCATATTTACCTAGTCTGCATGCAGTGCATGCACATGCAGTCATG

TCGTGCTAATGTGTAAAACATGTACATGCAGATTGCTGGGGGTGCAGGGGGCGGAGCCACCCTGTCCATG

CGGGGTGTGGGGCTTGCCCCGCCGGTACAGACAGTGAGCACCGGGGCACCTAGTCGCGGATACCCCCCCT

AGGTATCGGACACGTAACCCTCCCATGTCGATGCAAATCTTTAACATTGAGTACGGGTAAGCTGGCACGC

ATAGCCAAGCTAGGCGGCCACCAAACACCACTAAAAATTAATAGTCCCTAGACAAGACAAACCCCCGTGC

GAGCTACCAACTCATATGCACGGGGGCCACATAACCCGAAGGGGTTTCAATTGACAACCATAGCACTAGC

TAAGACAACGGGCACAACACCCGCACAAACTCGCACTGCGCAACCCCGCACAACATCGGGTCTAGGTAAC

ACTGAAATAGAAGTGAACACCTCTAAGGAACCGCAGGTCAATGAGGGTTCTAAGGTCACTCGCGCTAGGG

CGTGGCGTAGGCAAAACGTCATGTACAAGATCACCAATAGTAAGGCTCTGGCGGGGTGCCATAGGTGGCG

CAGGGACGAAGCTGTTGCGGTGTCCTGGTCGTCTAACGGTGCTTCGCAGTTTGAGGGTCTGCAAAACTCT

CACTCTCGCTGGGGGTCACCTCTGGCTGAATTGGAAGTCATGGGCGAACGCCGCATTGAGCTGGCTATTG

-continued

CTACTAAGAATCACTTGGCGGCGGGTGGCGCGCTCATGATGTTTGTGGGCACTGTTCGACACAACCGCTC

ACAGTCATTTGCGCAGGTTGAAGCGGGTATTAAGACTGCGTACTCTTCGATGGTGAAAACATCTCAGTGG

AAGAAAGAACGTGCACGGTACGGGGTGGAGCACACCTATAGTGACTATGAGGTCACAGACTCTTGGGCGA

ACGGTTGGCACTTGCACCGCAACATGCTGTTGTTCTTGGATCGTCCACTGTCTGACGATGAACTCAAGGC

GTTTGAGGATTCCATGTTTTCCCGCTGGTCTGCTGGTGTGGTTAAGGCCGGTATGGACGCGCCACTGCGT

GAGCACGGGGTCAAACTTGATCAGGTGTCTACCTGGGGTGGAGACGCTGCGAAAATGGCAACCTACCTCG

CTAAGGGCATGTCTCAGGAACTGACTGGCTCCGCTACTAAAACCGCGTCTAAGGGGTCGTACACGCCGTT

TCAGATGTTGGATATGTTGGCCGATCAAAGCGACGCCGGCGAGGATATGGACGCTGTTTTGGTGGCTCGG

TGGCGTGAGTATGAGGTTGGTTCTAAAAACCTGCGTTCGTCCTGGTCACGTGGGGCTAAGCGTGCTTTGG

GCATTGATTACATAGACGCTGATGTACGTCGTGAAATGGAAGAAGAACTGTACAAGCTCGCCGGTCTGGA

AGCACCGGAACGGGTCGAATCAACCCGCGTTGCTGTTGCTTTGGTGAAGCCCGATGATTGGAAACTGATT

CAGTCTGATTTCGCGGTTAGGCAGTACGTTCTCGATTGCGTGGATAAGGCTAAGGACGTGGCCGCTGCGC

AACGTGTCGCTAATGAGGTGCTGGCAAGTCTGGGTGTGGATTCCACCCCGTGCATGATCGTTATGGATGA

TGTGGACTTGGACGCGGTTCTGCCTACTCATGGGGACGCTACTAAGCGTGATCTGAATGCGGCGGTGTTC

GCGGGTAATGAGCAGACTATTCTTCGCACCCACTAAAAGCGGCATAAACCCCGTTCGATATTTTGTGCGA

TGAATTTATGGTCAATGTCGCGGGGGCAAACTATGATGGGTCTTGTTGTTGGCGTCCCGGAAAACGATTC

CGAAGCCCAACCTTTCATAGAAGGCGGCGGTGGAATCGAAATCTCGTGATGGCAGGTTGGGCGTCGCTTG

GTCGGTCATTTCGAAGGGCACCAATAACTGCCTTAAAAAAATTACGCCCCGCCCTGCCACTCATCGCAGT

ACTGTTGTAATTCATTAAGCATTCTGCCGACATGGAAGCCATCACAAACGGCATGATGAACCTGAATCGC

CAGCGGCATCAGCACCTTGTCGCCTTGCGTATAATATTTGCCCATGGTGAAAACGGGGGCGAAGAAGTTG

TCCATATTGGCCACGTTTAAATCAAAACTGGTGAAACTCACCCAGGGATTGGCTGAGACGAAAAACATAT

TCTCAATAAACCCTTTAGGGAAATAGGCCAGGTTTTCACCGTAACACGCCACATCTTGCGAATATATGTG

TAGAAACTGCCGGAAATCGTCGTGGTATTCACTCCAGAGCGATGAAAACGTTTCAGTTTGCTCATGGAAA

ACGGTGTAACAAGGGTGAACACTATCCCATATCACCAGCTCACCGTCTTTCATTGCCATACGTAACTCCG

GATGAGCATTCATCAGGCGGGCAAGAATGTGAATAAAGGCCGGATAAAACTTGTGCTTATTTTTCTTTAC

GGTCTTTAAAAAGGCCGTAATATCCAGCTGAACGGTCTGGTTATAGGTACATTGAGCAACTGACTGAAAT

GCCTCAAAATGTTCTTTACGATGCCATTGGGATATATCAACGGTGGTATATCCAGTGATTTTTTTCTCCA

TTTTAGCTTCCTTAGCTCCTGAAAATCTCGTCGAAGCTCGGCGGATTTGTCCTACTCAAGCTGATCCGAC

AAAATCCACACATTATCCCAGGTGTCCGGATCGGTCAAATACGCTGCCAGCTCATAGACCGTATCCAAAG

CATCCGGGGCTGATCCCCGGCGCCAGGGTGGTTTTTCTTTTCACCAGTGAGACGGGCAACAGCATACGCA

AACCGCCTCTCCCCCCTCCGTTGAAAACTAAAAAGCTGGGAAGGTGAATCGAATTTCGGGGCTTTAAAGC

AAAAATGAACAGCTTGGTCTATAGTGGCTAGGTACCCTTTTTGTTTTGGACACATGTAGGGTGGCCGAAA

CAAAGTATGGCAGGAAAAATTATTCGATGAGTGGCCTGATATGGTGCGTTGCAAACACCTCCTGTACACA

GGCGAGAATTTTAGGAATGTAATTACTGTGGTCCATATTTCGCACCGCGAGTGAAATTGGGCTATAGGCA

TCATCATCTAAAATTGGAATATAAAGTAGATTCTTCACCCCAATATCCATGGCAGACGCCGGTACGATGC

AGACGCCTTCACCTGCTGCCACCAAGCCGAGTGCCAGTTGAATTTCTCGAATTTCGGTGAGTTTGGATGG

TACTAGGCCTAGTTCGGTAAAGAGTGACTGAATAAAGGTCGCAAAATTGGGCTTTTGAGAGACTGGGTAC

AGCAGCATCGGTTCATCAATAATTTGAGAGAGATGAACCCCTGTTGCTGCAAACTGATTGAGGTGATGAT

GCTTATGGATTGCAAGTTTGAGCTGTTCTTTATGCAACACGATACGTCGAATTGCAGGATCGGTAATTTT

GAGCCGACCAAAACCCAGGTCTATTTTTCCCTGCTTAAGGGCATTAATTTGATCTTTGGTGCCGCATTCG

-continued

ATGAGTTCGATGTGAATTTCAGGATTTTGTTGACGAAACAGATAAATAATTTCAGGTAACAAACCATACA

GTAAGGAGCTGACGTAACCAATTCTCAAGGTTTGACTGACCGTTGCAATCCGTTTTGCCATTGAGGACGC

TTGTGCAGTATGAGTCAAAATCTGCACAGCATGCTGATAAAAAAACATGCCTGCTTCAGTCACTTTAGCC

GGTCTGAAGCCGCGTTCAAATAGTTGGATACCCAATTCTTCTTCGAGTTTTTGAATTTGTCGGCTGAGGG

GCGGCTGGGCAATACACAACTTTTCAGCAGCTTTGGAAATGCTTTGCTCTTCAACCACGGTCACAAAATA

TCTGAGGTGTCTTAGTTCCATTTATACGCCCTAATTGGTTTTATATACCTTTTTAGTATGCAAAAATACC

AAATTGGTATTTGTTTTTATTATTACATTCATTTAAAGTATGTAAATAGTATTTATTGAAAAGGAGATAT

ACAT*ATGGCTAGCAAAGGAGAAGAACTTTTCACGGGAGTTGTCCCAATTCTTGTTGAATTAGATGGTGAT*

*GTTAATGGGCACAAATTTTCTGTCCGTGGAGAGGGTGAAGGTGATGCTACAAACGGAAAACTCACCCTTA*

*AATTTATTTGCACTACTGGAAAACTACCTGTTCCATGGCCAACACTTGTCACTACTCTGACCTATGGTGT*

*TCAATGCTTTTCCCGTTATCCGGATCACATGAAACGGCATGACTTTTTCAAGAGTGCCATGCCCGAAGGT*

*TATGTACAGGAACGCACTATATCTTTCAAAGATGACGGGACCTACAAGACGCGTGCTGAAGTCAAGTTTG*

*AAGGTGATACCCTTGTTAATCGTATCGAGTTAAAGGGTATTGATTTTAAAGAAGATGGAAACATTCTTGG*

*ACACAAACTCGAGTACAACTTTAACTCACACAATGTATACATCACGGCAGACAAACAAAAGAATGGAATC*

AAAGCTAACTTCAAAATTCGCCACAACGTTGAAGATGGTTCCGTTCAACTAGCAGACCATTATCAACAAA

*ATACTCCAATTGGCGATGGCCCTGTCCTTTTACCAGACAACCATTACCTGTCGACACAATCTGTCCTTTC*

*GAAAGATCCCAACGAAAAGCGTGACCACATGGTCCTTCTTGAGTTTGTAACTGCTGCTGGGATTACACAT*

*GGCATGGATGAGCTCTACAAA*GGTGGCGGTTCTGAATTCACACCTAGGTAACCAGGCATCAAATAAAACG

AAAGGCTCAGTCGAAAGACTGGGCCTTTCGTTTTATCTGTTGTTTGTCGGTGAACGCTCTCTACTAGAGT

CACACTGGCTCACCTTCGGGTGGGCCTTTCTGCGTTTATAGATGTTGGTTCTTTCCTAAAGTTG

SEQ ID NO: 7 is the amino acid sequence of an exemplary *A. baylyi* CatM protein.

MELRHLRYFVTVVEEQSISKAAEKLCIAQPPLSRQIQKLEEELGIQLFE

RGERPAKVTEAGMFFYQHAVQILTHTAQASSMAKRIATVSQTLRIGYVS

SLLYGLLPEIIYLFRQQNPEIHIELIECGTKDQINALKQGKIDLGFGRL

KITDPAIRRIVLHKEQLKLAIHKHHHLNQFAATGVHLSQIIDEPMLLYP

VSQKPNFATFIQSLFTELGLVPSKLTEIREIQLALGLVAAGEGVCIVPA

SAMDIGVKNLLYIPILDDDAYSPISLAVRNMDHSNYIPKILACVQEVFA

THHIRPLIE

SEQ ID NO: 8 is an exemplary nucleic acid sequence encoding a sfgfp reporter:

ATGGCTAGCAAAGGAGAAGAACTTTTCACGGGAGTTGTCCCAATTCTTG

TTGAATTAGATGGTGATGTTAATGGGCACAAATTTTCTGTCCGTGGAGA

GGGTGAAGGTGATGCTACAAACGGAAAACTCACCCTTAAATTTATTTGC

ACTACTGGAAAACTACCTGTTCCATGGCCAACACTTGTCACTACTCTGA

CCTATGGTGTTCAATGCTTTTCCCGTTATCCGGATCACATGAAACGGCA

TGACTTTTTCAAGAGTGCCATGCCCGAAGGTTATGTACAGGAACGCACT

ATATCTTTCAAAGATGACGGGACCTACAAGACGCGTGCTGAAGTCAAGT

TTGAAGGTGATACCCTTGTTAATCGTATCGAGTTAAAGGGTATTGATTT

-continued

TAAAGAAGATGGAAACATTCTTGGACACAAACTCGAGTACAACTTTAAC

TCACACAATGTATACATCACGGCAGACAAACAAAAGAATGGAATCAAAG

CTAACTTCAAAATTCGCCACAACGTTGAAGATGGTTCCGTTCAACTAGC

AGACCATTATCAACAAAATACTCCAATTGGCGATGGCCCTGTCCTTTTA

CCAGACAACCATTACCTGTCGACACAATCTGTCCTTTCGAAAGATCCCA

ACGAAAAGCGTGACCACATGGTCCTTCTTGAGTTTGTAACTGCTGCTGG

GATTACACATGGCATGGATGAGCTCTACAAA

SEQ ID NO: 9 is the nucleic acid sequence of a portion of a modified $P_{cat}$; promoter, encompassing −35/−10 sites:

GTATTTGTTTTTATTATTACATTCATTTAAAGTA

SEQ ID NO: 10 is the nucleic acid sequence of $P_{cat}$-opt-2, an exemplary $P_{cat}$; promoter optimized for *C. glutamicum*:

TTATACGCCCTAATTGGTTTTATATACCTTTTTAGTATGCAAAAATACC

AAATTGGTATTTGTTTTTATTATTACATTCATTTAAAGTATGTAAATAG

TATTTATTGAAAAGGAGATATACAT

SEQ ID NO: 11 is the nucleic acid sequence of a portion of an additional modified $P_{cat}$; promoter:

GTATTTGTTTTTATTATTACATACATTTACTGTA

SEQ ID NO: 12 is a nucleic acid sequence encoding an exemplary *A. baylyi* CatM protein (reverse complement):

TTATTCGATGAGTGGCCTGATATGGTGCGTTGCAAACACCTCCTGTACA

CAGGCGAGAATTTTAGGAATGTAATTACTGTGGTCCATATTTCGCACCG

CGAGTGAAATTGGGCTATAGGCATCATCATCTAAAATTGGAATATAAAG

TAGATTCTTCACCCCAATATCCATGGCAGACGCCGGTACGATGCAGACG

CCTTCACCTGCTGCCACCAAGCCGAGTGCCAGTTGAATTTCTCGAATTT

CGGTGAGTTTGGATGGTACTAGGCCTAGTTCGGTAAAGAGTGACTGAAT

AAAGGTCGCAAAATTGGGCTTTTGAGAGACTGGGTACAGCAGCATCGGT

TCATCAATAATTTGAGAGAGATGAACCCCTGTTGCTGCAAACTGATTGA

GGTGATGATGCTTATGGATTGCAAGTTTGAGCTGTTCTTTATGCAACAC

GATACGTCGAATTGCAGGATCGGTAATTTTGAGCCGACCAAAACCCAGG

TCTATTTTTCCCTGCTTAAGGGCATTAATTTGATCTTTGGTGCCGCATT

CGATGAGTTCGATGTGAATTTCAGGATTTTGTTGACGAAACAGATAAAT

AATTTCAGGTAACAAACCATACAGTAAGGAGCTGACGTAACCAATTCTC

AAGGTTTGACTGACCGTTGCAATCCGTTTTGCCATTGAGGACGCTTGTG

CAGTATGAGTCAAAATCTGCACAGCATGCTGATAAAAAAACATGCCTGC

TTCAGTCACTTTAGCCGGTCTGAAGCCGCGTTCAAATAGTTGGATACCC

AATTCTTCTTCGAGTTTTTGAATTTGTCGGCTGAGGGGCGGCTGGGCAA

TACACAACTTTTCAGCAGCTTTGGAAATGCTTTGCTCTTCAACCACGGT

CACAAAATATCTGAGGTGTCTTAGITCCAT

DETAILED DESCRIPTION cis,cis-Muconic acid is an important industrial precursor, used for the production of adipic acid and terephthalic acid, which are in turn used for production of nylon and polyethylene terephthalate (PET), respectively. While several microbial chassis have been explored for metabolic engineering to produce muconate from renewable feedstocks, such as sugars or lignin derived from biomass, *Corynebacterium glutamicum* has an advantage due to its ability to grow in an acidic environment. Microbial engineering and optimization of strains for high titer, yield, and rate need high throughput testing tools. Provided herein are biosensors that can detect production of muconate and provide a reporter signal, such as in the form of fluorescence. When coupled to a high throughput detection and sorting system such as flow cytometry, more than 100,000 variants can be screened in a matter of minutes (Jha et al., *Nucl. Acids Res.* 42:8150-8160, 2014). As a result, metabolic pathways and whole genomes of *C. glutamicum* can be rapidly optimized for production of muconate.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. All database accession numbers (such as GenBank or UniProt accession numbers) are incorporated herein by reference in their entirety, as present in the database on Nov. 3, 2021. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Biosensor: A biological molecule (such as a nucleic acid, peptide, or protein) that can detect a change in environment, for example, in a dose-dependent manner. In some examples, a biosensor includes a protein (such as a transcription factor) that can sense a change in concentration of a small molecule in or around a cell. The biosensor may be coupled (directly or indirectly) to a reporter, including but not limited to an antibiotic resistance gene (such as a gene encoding a β-lactamase), a gene encoding a fluorescent protein (such as a green fluorescent protein), or a metabolic gene (such as lacZ). The reporter then indicates the presence and/or amount of the detected molecule, for example, by antibiotic resistance, fluorescence, or color change.

CatM: A transcription factor belonging to LysR family from *Acinetobacter* baylyi (e.g., *A. baylyi* ADP1). CatM binds to cis,cis-muconic acid and regulates the metabolism of the molecule by activating cat gene expression. The GenBank Accession number P07774 is an exemplary wild-type CatM amino acid sequence.

cis,cis-muconic acid (ccMA): Also referred to as muconate. A precursor of adipic acid, which is utilized for nylon 6,6 production, and of terephthalic acid, which is used for polyethylene terephthalate (PET) production for bottles and textiles. ccMA has the structure:

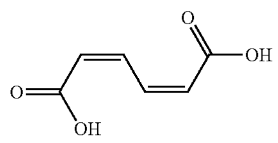

*Corynebacterium glutamicum*: A non-pathogenic gram-positive rod-shaped bacterium that was originally identified as secreting glutamate and is currently used industrially for the production of several amino acids. An exemplary *C. glutamicum* genome sequence is GenBank Accession No. NZ_CP025533.

Heterologous: Originating from a different genetic source or species. A gene or nucleic acid that is heterologous to a prokaryotic cell originates from an organism or species other than the prokaryotic cell in which it is expressed or in a different genetic location, orientation, or in any other way modified from its natural sequence and location in the genome. Methods for introducing a heterologous gene or nucleic acid in a cell or organism are well known in the art, for example transformation with a nucleic acid, including electroporation, lipofection, particle gun acceleration, and homologous recombination.

Isolated: An "isolated" biological component (such as a nucleic acid molecule, protein, or cell) has been substantially separated or purified away from other biological components in the cell of the organism, or the organism itself, in which the component occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

It is understood that the term "isolated" does not imply that the component is free of trace contamination, and can include molecules that are at least 50% isolated, such as at least 50%, 55%, 60%, 65%, 70%, 75%, 80%, 85%, 90%, 95%, 98%, 99%, or even 100% isolated.

Modified: A "modified" nucleic acid or polypeptide is one that has a sequence that is not naturally occurring or has a sequence that is made by an artificial combination of two or more otherwise separated segments of sequence. A modified nucleic acid or polypeptide may be produced by chemical synthesis or artificial manipulation of isolated segments of nucleic acids, e.g., by genetic engineering or genetic editing techniques.

Operably linked: A first nucleic acid is operably linked to a second nucleic acid when the first nucleic acid is placed in a functional relationship with the second nucleic acid. For instance, a regulatory element is operably linked to a coding sequence if the regulatory element affects the transcription or expression of the coding sequence. Regulatory elements include regions such as promoters or portions thereof (such as −35 and/or −10 sites), transcription factor binding sites, operators, terminators and the like, that may be located upstream or downstream of a coding sequence.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Transduced and Transformed: A vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in Gram negative and Gram positive bacterial cells. Exemplary vectors include those for use in *E. coli, P. putida, A. baylyi*, and *C. glutamicum.*

II. Muconate Biosensors

Figure 1:
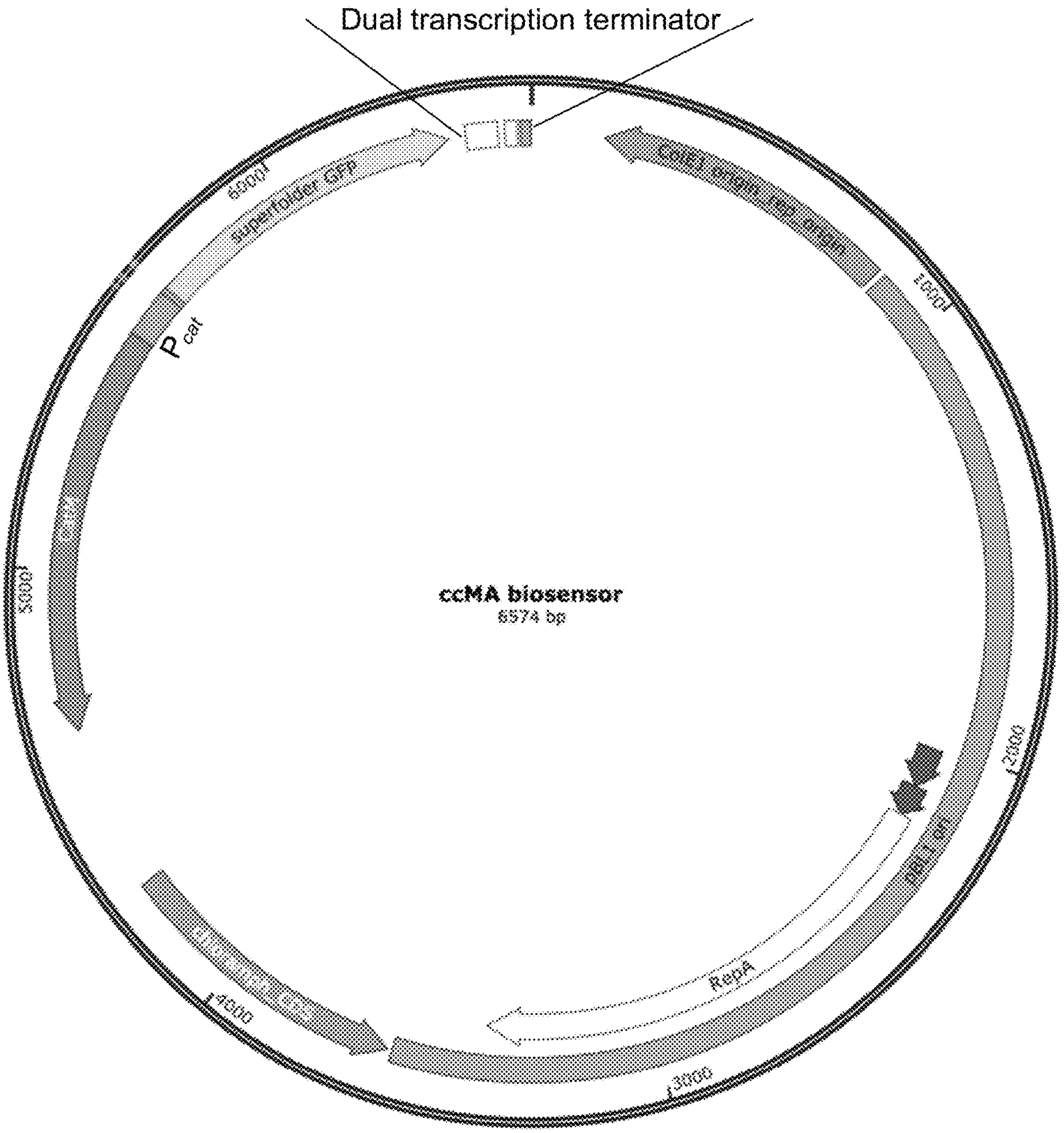
FIG. 1 is a schematic diagram of an exemplary plasmid including a *C. glutamicum* muconate biosensor. The plasmid pRJ2010 includes a $P_{cat}$ promoter from *Acinetobacter baylyi* ADP1 optimized for use in *C. glutamicum* arranged between the transcription factor catM and reporter sfgfp (encoding superfolder GFP) genes.
Figure 2:
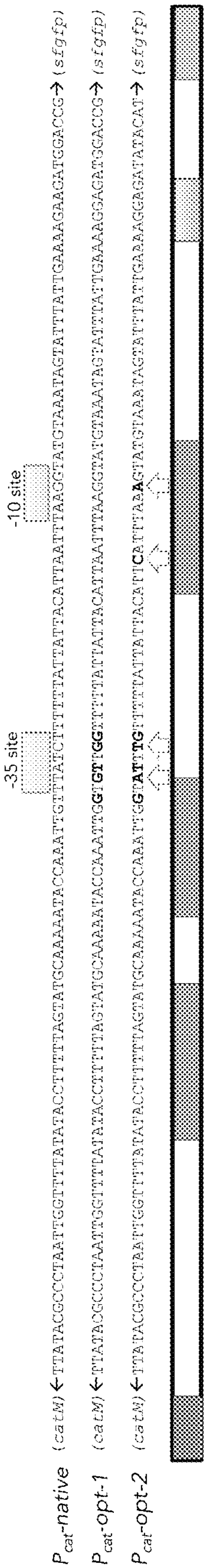
FIG. 2 shows the sequence of three generations of $P_{cat}$ promoter regions. Top: native *A. baylyi* ADP1 $P_{cat}$ sequence (SEQ ID NO: 1); Middle: $P_{cat}$ sequence optimized for *Pseudomonas putida* ($P_{cat}$-opt-1; SEQ ID NO: 2); Bottom.

Disclosed herein are biosensors for cis,cis-muconic acid. In some embodiments, the biosensors include a nucleic acid encoding a CatM protein, a promoter regulated by cis,cis-muconic acid (such as a CatM-regulated promoter; $P_{cat}$), and in some examples, a nucleic acid encoding a reporter. The nucleic acid encoding the reporter protein is operably linked to the promoter. In some embodiments, the CatM-encoding nucleic acid is also operably linked to the same promoter, but in other embodiments can be independently regulated from an independent promoter. A schematic diagram showing an exemplary cis,cis-muconic acid biosensor (in the context of a plasmid vector) is illustrated in FIG. 1. The promoter ($P_{cat}$) includes three CatM operator sites (CatMO; FIG. 2). In the repressed state, CatM binds to the operator at sites 1 and 3. Upon binding to muconate, CatM binds to sites 1 and 2, exposing the −10 and −35 sites to RNA polymerase (Ezezika et al., *Appl. Environ. Microbiol.* 72:1749-1758, 2006). In particular embodiments, the promoter includes one or more modifications from a naturally occurring promoter, for example, to improve its function in *Corynebacterium glutamicum*. In some examples, the CatM promoter ($P_{cat}$) is modified from a naturally occurring $P_{cat}$ from *Acinetobacter baylyi.*

In some embodiments, the biosensor includes a nucleic acid encoding a CatM protein operably linked to a regulatory element including a modified $P_{cat}$ promoter, wherein the modified $P_{cat}$ promoter includes a nucleic acid sequence with at least 95% sequence identity (such as at least 95%, at least 96%, at least 97%, at least 98%, or at least 99% sequence identity) to SEQ ID NO: 9 or the complement thereof. The modified $P_{cat}$ promoter is capable of producing a response in the presence of ccMA or ccMA precursors (e.g., benzoate or catechol). In some examples, the biosensor includes a modified $P_{cat}$ promoter including a nucleic acid sequence including the nucleic acid sequence of SEQ ID NO: 9 or the complement thereof. In other examples, the modified $P_{cat}$ promoter includes a nucleic acid sequence with at least 90% sequence identity (such as at least 91%, 92%, 93%, 94%, 95%, 96%, 97%, 98%, 99%, or more sequence identity) to SEQ ID NO: 10. In other examples, the promoter includes or consists of the nucleic acid sequence of SEQ ID NO: 10 or the complement thereof.

In other embodiments, the cis,cis-muconic acid biosensor includes a CatM protein operably linked to a regulatory element including a modified $P_{cat}$ promoter including a nucleic acid sequence with at least 95% sequence identity (such as at least 95%, at least 96%, at least 97%, at least 98%, or at least 99% sequence identity) to SEQ ID NO: 11 or the complement thereof. In other examples, the promoter includes the nucleic acid sequence of SEQ ID NO: 11. In some examples, the promoter includes a nucleic acid sequence with at least 90% sequence identity (such as at least 91%, 92%, 93%, 94%, 95%, 96%, 97%, 98%, 99%, or 100% identity) to the nucleic acid sequence of SEQ ID NO: 4 or the complement thereof. In other examples, the promoter includes or consists of the nucleic acid sequence of SEQ ID NO: 4 or the complement thereof.

In some examples, the CatM protein encoded by the biosensor is an *Acinetobacter baylyi* CatM protein. In some examples, the CatM protein is encoded by a nucleic acid sequence with at least 90% sequence identity (such as at least 91%, 92%, 93%, 94%, 95%, 96%, 97%, 98%, 99%, or 100% identity) to the nucleic acid sequence of SEQ ID NO: 12. In some examples, the CatM protein includes one or more amino acid substitutions compared to the wild type protein. For example, the CatM protein may include an amino acid substitution at one or more of amino acid positions corresponding to amino acids 97, 127, 128, and 147 of SEQ ID NO: 7 (such as one or more of V97I, G127A, T128A and L147V).

In some embodiments, the biosensor includes a nucleic acid encoding a reporter protein operably linked to the modified Pear promoter. The reporter encodes a protein that generates a detectable output, such as an antibiotic resistance (e.g., genes for β-lactamase, streptomycin or kanamycin), fluorescence, bioluminescence (such as gene for a luciferase) or a color (such as gene for LacZ). In some examples, the reporter encodes a fluorescent protein, such as a green fluorescent protein (GFP). In one example, the reporter encodes a superfolder GFP (sfGFP). Other GFPs or related fluorescent proteins (such as eGFP, red fluorescent protein (RFP), superfolder RFP (sfRFP), mCherry, sfCherry, mStrawberry, mOrange, or dTomato) can also be used as a reporter in the disclosed biosensors. In some examples, the reporter is a sfGFP and the protein is encoded by a nucleic acid sequence with at least 90% sequence identity (such as at least 91%, 92%, 93%, 94%, 95%, 96%, 97%, 98%, 99%, or 100% identity) to the nucleic acid sequence of SEQ ID NO: 8.

In some embodiments, the cis,cis-muconic acid biosensors provided herein are incorporated into a vector, into an autonomously replicating plasmid or virus, or into the genomic DNA of a host cell, or which exists as a separate molecule independent of other sequences. In some examples, the vector including the biosensor includes a nucleic acid sequence with at least 95% sequence identity (such as at least 95%, at least 96%, at least 97%, at least 98%, or at least 99% sequence identity) to SEQ ID NO: 9 or SEQ ID NO: 11 or includes the nucleic acid sequence of SEQ ID NO: 9 or SEQ ID NO: 11. In other examples, the including the vector including the biosensor includes a nucleic acid sequence with at least 95% sequence identity (such as at least 95%, at least 96%, at least 97%, at least 98%, or at least 99% sequence identity) to SEQ ID NO: 10 or SEQ ID NO: 4 or includes the nucleic acid sequence of SEQ ID NO: 10 or SEQ ID NO: 4. In some examples, the vector includes a nucleic acid sequence with at least 90% identity (such as at least 91%, 92%, 93%, 94%, 95%, 96%, 97%, 98%, 99%, or 100% identity) to the nucleic acid sequence of SEQ ID NO: 5 or the complement thereof. In other examples, the vector includes a nucleic acid sequence with at least 95% identity (such as at least 95%, 96%, 97%, 98%, 99%, or 100% identity) to SEQ ID NO: 6 or the complement thereof. In other examples, the vector includes or consists of the nucleic acid sequence of SEQ ID NO: 6.

In some non-limiting examples, the vector also includes one or more of an origin of replication, a nucleic acid encoding a replication initiator protein (such as RepA or a temperature-sensitive RepA), a nucleic acid encoding an antibiotic resistance gene (such as chloramphenicol resistance or apramycin resistance), a transcription terminator (such as a dual transcription terminator), or other features. In particular examples, the vector encodes a replicase. One of ordinary skill in the art will recognize that these portions of the vector can be altered (for example, modified or replaced) with other appropriate components.

Vectors for cloning, replication, and/or expression of the disclosed nucleic acid molecules include bacterial plasmids, such as bacterial cloning or expression plasmids. Exemplary bacterial plasmids into which the nucleic acids can be cloned include *E. coli* plasmids, such as pBR322, pUC plasmids (such as pUC18 or pUC19), pBluescript. pACYC184, pCD1, pGEM® plasmids (such as pGEM®-3, pGEM®-4, pGEM-T® plasmids; Promega, Madison, WI), TA-cloning vectors, such as pCR® plasmids (for example, pCR® II, pCR® 2.1, or pCR® 4 plasmids; Life Technologies, Grand Island, NY) or pcDNA plasmids (for example pcDNA™3.1 or pcDNA™3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can also be cloned into *B. subtilis* plasmids, for example, pTA1060 and pHT plasmids (such as pHT01, pHT43, or pHT315 plasmids). In some examples, the vector is a broad host range vector, such as pBTBX vectors (Prior et al., *Biotechnol. Bioeng.* 106:326-332, 2010), pBTL vectors (Lynch et al., *Biotechnol. Bioeng.* 94:151-158, 2006), or BAVIK vectors (Murin et al., *Appl. Env. Microbiol.* 78:280-283, 2012). In some examples, the vector is based on vector pBTL-2 (Addgene plasmid #22806) or vector pBAVIK-PT5-gfp (Addgene plasmid #26702), or pCRA1 (Kotrba et al., *Biochem. Biophys. Res. Commun.* 289:1307-1313, 2001) or pSFK6 (Nakamura et al., *Plasmid* 56:179-186, 2006), or pBL1 or pUL330 (Santamaria et al, *J. Gen. Microbiol.* 130:2237-2246, 1984), or pEKO or pEKEx1 (Eikmanns et al., *Gene* 102:93-98, 1991) or their derivatives such as pEKEx2 (JBEI-7909) and pEKEx3.

III. Host Cells

Also provided are host cells including a nucleic acid including one or more of the disclosed cis,cis-muconic acid biosensors or vectors including one or more of the disclosed cis,cis-muconic acid biosensors. In some embodiments, the cells are bacterial cells. Bacterial cells are available from numerous sources, including commercial sources known to those skilled in the art, such as the American Type Culture Collection (ATCC; Manassas, VA). Commercial sources of cells used for recombinant protein expression also provide instructions for usage of such cells.

In particular non-limiting examples, the bacterial cells are *Corynebacterium glutamicum* cells. In one example, the cells are *C. glutamicum* strain 534 cells (ATCC 13032; see also U.S. Pat. No. 3,002,889). In some examples, the *C. glutamicum* cells are modified to increase accumulation of cis,cis-muconic acid in the cells. In some examples, the cells have an inactive or deleted catB gene, which decreases or prevents conversion of cis,cis-muconic acid to muconolactone. In other examples, the cells include overexpression of the catA gene, which increases conversion of catechol to cis,cis-muconic acid. In some other examples, the cells include overexpression of the qsuB gene or a heterologous dehydroshikimate dehydratase gene (such as asbF from *Bacillus cereus* or *Bacillus thuringiensis*) along with a heterologous gene for protocatechuate decarboxylase (such as aroY from *Enterobacter cloacae*) to convert a metabolic intermediate dehydroshikimate (in shikimate pathway) to catechol.

In some examples, the cis,cis-muconic acid biosensor nucleic acid or vector including the cis,cis-muconic acid biosensor nucleic acid is introduced extrachromosomally and replicated within the host cell. In other examples, after introduction of the plasmid, a double homologous recombination event occurs and the one or more genes are inserted into the genome of the host cell.

Transformation of a bacterial cell with recombinant DNA can be carried out by techniques known to those skilled in the art. Where the host is bacterial, competent cells which are capable of DNA uptake can be prepared from cells harvested after exponential growth phase and subsequently treated by the $CaCl_2$) method using procedures well known in the art. Alternatively, $MgCl_2$ or RbCl can be used. Bacteria can also be transformed by methods including heat shock, electroporation, conjugation, or transduction.

IV. Methods of Use

Also disclosed herein are methods of utilizing the disclosed cis,cis-muconic acid biosensors or cells expressing the disclosed cis,cis-muconic acid biosensors. In some embodiments, the methods include detecting production of cis,cis-muconic acid in a sample. In other embodiments, the methods include detecting presence of cis,cis-muconic acid in the environment of a cell.

In some examples, the methods can be used to detect or identify improved or increased production of cis,cis-muconic acid by a cell and/or improved or increased transport of cis,cis-muconic acid into the cell. For example, cells including the cis,cis-muconic acid biosensor can be transformed with one or more variants (such as a library of variants) of one or more of the enzymes involved in production of cis,cis-muconic acid (such as DAHP synthase (encoded by aroG or homologs), dehydroshikimate dehydratase (encoded by qsuB or asbF), PCA decarboxylase (encoded by aroY), catechol 1,2-dioxygenase (encoded by catA), benzoate 1,2-dioxygenase (encoded by benABC), or benzoate 1,2-cis-dihydrodiol dehydrogenase (encoded by benD)) and can be screened for increased production of cis,cis-muconic acid, to identify variants with desirable properties. In other embodiments, the genome of cells including the biosensor can be mutated (for example by chemical or ultraviolet mutagenesis) in order to produce a population of cells with a plurality of genotypic variants. Cells that have improved or increased production of cis,cis-muconic acid can be selected and isolated, for example, based on detection of increased reporter output.

In some examples, bacterial cells (e.g., *C. glutamicum* cells) are transformed with a vector including a disclosed biosensor. In other examples, the cells are transformed with variants of the biosensor (such as a library encoding variants of the biosensor). The cells are screened for presence and/or amount of cis,cis-muconic acid by detecting output of the reporter, such as fluorescence. In some examples, cells including a disclosed biosensor are cultured under conditions sufficient for detection of cis,cis-muconic acid or production of cis,cis-muconic acid and output of the reporter is detected. In some examples, the cells are cultured in the presence of a precursor of muconate in *C. glutamicum*, such as benzoate or catechol. In one example, the reporter is a fluorescent protein (such as a GFP, for example, sfGFP), and fluorescence is detected.

Samples can be screened for production of or presence of cis,cis-muconic acid via either flow cytometry or a fluorescence microplate reader (Jha et al., *Nucl. Acids Res.* 42:8150-8160, 2014) or on a solid growth media (e.g., petri dish; Jha et al., *ACS Syn. Biol.* 9:1234-1239, 2020) and selection based on the fluorescence of the individual cell (for flow cytometry or a fluorescence microplate reader) or fluorescence (or other visually detectable signal) of the colonies on a solid growth media. If the reporter gene in the sensor plasmid is a survival enhancing gene (for example the protein product of the gene provides resistance to a suitable antibiotic or the protein product of the gene provides a suitable nutrient to the auxotroph), the screening can be carried out based on growth characteristics, such as the growth rate. If the reporter gene is for a hydrolytic enzyme (for example lacZ), the colonies on a petri dish will produce intense blue color suitable for screening if the growth medium is supplemented with 5-bromo-4-chloro-3-indolyl-β-D galactopyranoside (X-gal).

EXAMPLES

The following examples are provided to illustrate certain particular features and/or embodiments. These examples should not be construed to limit the disclosure to the particular features or embodiments described.

Example 1

Generation of a Muconate Biosensor for Use in *Corynebacterium glutamicum*

A muconate biosensor was constructed using the muconate-responsive transcription factor CatM, such that transcription of a reporter (superfolder GFP; sfgfp) was under the control of a $P_{cat}$ promoter including three CatM binding sites, referred to as operator (CatMO). The $P_{cat}$ promoter was placed between the catM and sfgfp genes (FIG. 1). The $P_{cat}$ promoter from *Acinetobacter baylyi* was previously modified for use in *Pseudomonas putida* and was selected from a library of >65,000 promoter variants (Bentley et al., *Metabolic Engineering* 59:65-74, 2020). The modified $P_{cat}$ promoter, when transferred to *C. glutamicum* compatible vector (pBL1 ori), showed response in *C. glutamicum*. In order to optimize a $P_{cat}$ promoter for use in *C. glutamicum*, a plasmid library was created using the same >65,000 combinations in the promoter region cloned in the vector with pBL1 ori and was transformed in *C. glutamicum* ATCC 13032 strain with catB gene deletion. Using FACSAria III sorter (BD Biosciences), set at standard settings for GFP fluorescence (488 nm excitation laser and 530/30 nm band-pass emission filter), four rounds of sorting were performed to select for high GFP fluorescence response in the presence of benzoate (a precursor of muconate) and low background signal in the absence of any muconate precursor, to eliminate constitutive promoter.

A modified $P_{cat}$ promoter that was active in *C. glutamicum* was identified. The promoter included changes in the −35 and −10 sites, as well as other changes compared to the original *A. baylyi* $P_{cat}$ and the *P. putida* $P_{cat}$ (FIG. 2). As shown in FIG. 3, the *C. glutamicum* optimized promoter ($P_{cat}$-opt-2) showed lower background and a higher contrast ratio of >50-fold, while the *P. putida* optimized promoter ($P_{cat}$-opt-1) when transferred in *C. glutamicum*, had higher background and lower contrast ratio. The plasmid including catM-sfgfp sensor-reporter gene and Pear-opt-2 promoter was designated pRJ2010.

Example 2

Characterization of a Muconate Biosensor

*C. glutamicum* ATCC 13032 (AcatB) strain including plasmid pRJ2010 was designated RJ95A and stored as glycerol stocks. For characterization, RJ95A was grown overnight from the glycerol stock in BHIS medium (brain heart infusion with sorbitol) supplemented with 10 µg/mL of chloramphenicol ($Cm_{10}$). The overnight seed culture was then transferred into fresh BHIS+$Cm_{10}$ media in a culture tube and grown to an OD (600 nm) of 0.6 at 30° C. and continuous shaking at 225 rpm. The culture was then split in a volume of 180 µL per well into a deep-well 96 well plate containing inducers (muconate or benzoate and catechol as muconate precursors, protocatechuate (PCA) as a negative control) to give a final concentration ranging from 0.01 mM to 10 mM in triplicate wells. The plate was incubated overnight at 1000 rpm and 30° C. in a deep-well maximizer shaker (Taitec Bioshaker MBR-022UP). In order to measure the fluorescence of the cells at different inducer concentration, 5 µL of overnight culture was diluted into 200 µL of 1×PBS (phosphate buffered saline) buffer and read using Accuri C6 (BD Biosciences) using standard setting for GFP fluorescence. The FSC/SSC (FSC measures forward scatter representing the size of the cell, and SSC measures side scatter representing the granularity of the cells) scatter plot was gated appropriately to represent *C. glutamicum* cells and mean fluorescence of the cells in the gate was noted as the biosensor response.

The biosensor (plasmid construct pCg_CatM_C2), when tested in ccMA accumulating strain (*C. glutamicum* 13032 AcatB), showed a clear dose-response with a ccMA precursor such as benzoate (FIGS. 5A and 5B). However, it also showed high background fluorescence and reduced contrast ratio (fold change in fluorescence over uninduced (UI)) compared to *P. putida* host (FIG. 3). A library of diversity >65,000, was under represented due to relatively lower transformation efficiency compared to *P. putida* in the experimental set up. Considering there were multiple solutions ($P_{cat}$ variants), as observed in the case of *P. putida*, growth, induction and FACS were then pursued using an under-represented 13032 library of ~35,000. Three rounds of positive selection (high fluorescence in the presence of 1 mM benzoate) and single negative selection (uninduced population with low background fluorescence) fetched multiple promising clones with contrast ratio >20 at ccMA precursors such as 1 mM benzoate or 1 mM catechol. A representative clone RJ95A (harboring biosensor plasmid pRJ2010) showed four new mutations in the promoter region and >65-fold contrast ratio at 1 mM catechol with lowest detected concentration <10 µM, and >40-fold contrast ratio at 1 mM benzoate with lowest detected concentration >30 µM (FIGS. 4A and 4B). In Gram negative bacteria such as *P. putida*, such a response was not observed with ccMA (FIG. 6).

At concentrations higher than 1 mM, the aromatic precursors most likely were toxic to the cells, resulting in drop in fluorescence response (FIGS. 4A, 5A). The negative control precursor, PCA, which does not have a metabolic route for conversion to ccMA in 13032 (absence of aroY), failed to show any visible response even at 10 mM concentration (FIG. 5A).

Example 3

Temperature Sensitive Biosensor for Rapid Curing

While biosensor tools provide advantages in elevating throughput to rapidly arrive to an optimized strain, it is necessary to cure the strain of the biosensor after the strain optimization efforts. In order to establish a protocol for curing strains of biosensor plasmid, the sensor-reporter cassette from the ccMA biosensor plasmid pRJ2010 was ported to a vector containing BL1's that consists of a replicase RepA with mutation Pro→Ser (Nakamura et al., Plasmid 56:179-186, 2006). The plasmid pJV4 (FIG. 7) including an apramycin resistance gene was tested in *C. glutamicum* AcatB strain. The fluorescence response from the ccMA biosensor was measured using catechol (a ccMA precursor), and the cells were challenged at 30° C. and 37° C. in the presence and absence of apramycin antibiotic. The fluorescence response from the ccMA biosensor determined the copy number of the plasmid in the strain. While 30° C. with apramycin condition showed highest stability of the plasmid in 13032 (FIGS. 8A and 8C), at an increased temperature such as 37° C., there was substantial decrease in fluorescence response of the population. Flow cytometry analysis showed heterogeneity in the population and a mix of reduced (possibly due to decrease in copy number of plasmid) and no fluorescence (plasmid cured) cells were observed (FIG. 8D). When the cells from a particular condition were regrown in the same condition, homogeneous population was observed at 30° C. with apramycin and strong GFP fluorescence retained (FIGS. 8B and 8E). At 37° C., the cell density was quite low both in the presence and absence of apramycin, but the cells were completely devoid of any green fluorescence (FIGS. 8B and 8F). Hence, here the biosensor activity was used to monitor self-curing (removal of a plasmid), that remains an important step to create clean strains that can be used for next metabolic engineering efforts or for production.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A cis,cis-muconic acid biosensor comprising a nucleic acid encoding a HTH-type transcriptional regulator CatM (CatM) protein operably linked to a regulatory element comprising a modified $P_{cat}$ promoter, wherein the modified $P_{cat}$ promoter comprises a nucleic acid sequence with at least 98% sequence identity to SEQ ID NO: 9 or SEQ ID NO: 11.

2. The cis,cis-muconic acid biosensor of claim 1, wherein the modified $P_{cat}$ promoter is capable of producing a response in the presence of cis,cis-muconic acid (ccMA) or a ccMA precursor.

3. The cis,cis-muconic acid biosensor of claim 1, wherein the modified $P_{cat}$ promoter comprises the nucleic acid sequence of SEQ ID NO: 9 or SEQ ID NO: 11.

4. The cis,cis-muconic acid biosensor of claim 3, wherein the modified $P_{cat}$ promoter comprises the nucleic acid sequence of SEQ ID NO: 10 or SEQ ID NO: 4.

5. The cis,cis-muconic acid biosensor of claim 1, further comprising a nucleic acid encoding a reporter protein operably linked to the modified $P_{cat}$ promoter.

6. The cis,cis-muconic acid biosensor of claim 5, wherein the reporter protein is a fluorescent protein.

7. The cis,cis-muconic acid biosensor of claim 1, wherein the biosensor comprises a nucleic acid sequence with at least 90% sequence identity to SEQ ID NO: 5 or the full complement thereof.

8. The cis,cis-muconic acid biosensor of claim 7, wherein the biosensor comprises the nucleic acid sequence of SEQ ID NO: 5 or the full complement thereof.

9. A vector comprising the cis,cis-muconic acid biosensor of claim 1.

10. The vector of claim 9, wherein the vector comprises the nucleic acid sequence of SEQ ID NO: 6.

11. A host cell comprising the cis,cis-muconic acid biosensor of claim 5.

12. A host cell comprising the vector of claim 9.

13. The host cell of claim 11, wherein the cell is a bacterial cell.

14. The host cell of claim 13, wherein the bacterial cell is a *Corynebacterium glutamicum* cell.

15. The host cell of claim 14, wherein the *C. glutamicum* cell comprises an inactive or deleted catB gene, an overexpressed catA gene, or both.

16. A method of detecting cis,cis-muconic acid, comprising:

culturing the host cell of claim 11 under conditions sufficient to detect cis,cis-muconic acid; and detecting output of the reporter protein.

17. The method of claim 16, wherein the reporter protein is a fluorescent protein, and detecting the output comprises detecting a fluorescence signal.

18. The method of claim 17, wherein detecting the fluorescence signal is by flow cytometry or using a fluorescence microplate reader.

19. The method of claim 16, wherein the cis,cis-muconic acid is produced by the cell, is present in the environment of the cell, or both.

* * * * *